US006265388B1

(12) United States Patent
Fett et al.

(10) Patent No.: US 6,265,388 B1
(45) Date of Patent: *Jul. 24, 2001

(54) ANTISENSE INHIBITION OF ANGIOGENIN EXPRESSION

(75) Inventors: James W. Fett, Waltham; Karen A. Olson, Brookline, both of MA (US)

(73) Assignee: President and Fellows of Harvard College, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/045,301

(22) Filed: Mar. 20, 1998

Related U.S. Application Data

(60) Provisional application No. 60/041,182, filed on Mar. 21, 1997.

(51) Int. Cl.[7] .............................. A61K 48/00; C12Q 1/68; C12N 15/85; C12N 15/11; C07H 21/04
(52) U.S. Cl. .................................. 514/44; 435/6; 435/325; 435/366; 435/369; 435/371; 435/375; 536/23.1; 536/24.3; 536/24.31; 536/24.33; 536/24.5
(58) Field of Search ........................... 435/6, 91.1, 440, 435/325, 366, 369, 371, 320.1; 536/23.1, 23.5, 24.3, 24.31, 24.33, 24.5; 514/44

(56) References Cited

U.S. PATENT DOCUMENTS

| 4,806,463 | 2/1989 | Goodchild et al. ...................... 435/5 |
| 4,916,073 | 4/1990 | Vallee et al. ....................... 435/252.3 |
| 4,966,849 | 10/1990 | Vallee et al. ........................... 435/199 |
| 5,004,810 | 4/1991 | Draper ................................ 536/24.5 |
| 5,087,617 | 2/1992 | Smith .................................... 514/44 |
| 5,098,890 | 3/1992 | Gewirtz et al. ....................... 514/44 |
| 5,135,917 | 8/1992 | Burch .................................... 514/44 |
| 5,135,919 | 8/1992 | Folkman et al. ....................... 514/56 |
| 5,166,195 | 11/1992 | Ecker .................................... 514/44 |
| 5,194,428 | 3/1993 | Agrawal et al. ...................... 514/44 |
| 5,270,204 | 12/1993 | Vallee et al. ....................... 435/252.3 |
| 5,286,717 | 2/1994 | Cohen et al. ......................... 514/44 |
| 5,442,049 | * 8/1995 | Anderson et al. .................. 536/24.5 |
| 5,563,255 | 10/1996 | Monia et al. ..................... 536/24.31 |
| 5,637,471 | * 6/1997 | Artavanis-Tsakonas et al. .. 435/7.23 |
| 5,639,725 | 6/1997 | O'Reilly et al. ...................... 514/12 |
| 5,698,586 | 12/1997 | Kishimoto et al. ................. 514/475 |
| 5,712,291 | 1/1998 | D'Amato ............................. 514/323 |

FOREIGN PATENT DOCUMENTS

| 0 291 686 A2 | 11/1988 | (EP) . |
| WO 96/40769 | 12/1996 | (WO) . |
| WO 97/00957 | 1/1997 | (WO) . |

OTHER PUBLICATIONS

Durnam, D.M. et al. Analytical Biochemistry 131, 385–393 (1983).*
Rybak, S.M. et al. Biochemical And Biophysical Research Communications, vol. 146, No. 3, pp. 1240–1248, Aug. 14, 1987.*
Weiner, H.L. et al. Science vol. 237, pp. 280–282, Jul. 17, 1987.*
Li, D. et al. Journal of Pathology, vol. 172: 171–175 (Feb. 1994).*
Branch, A.D. TIBS 23, Feb. 1998, pp. 45–50.*
Stein, C.A. Nature Biotechnology, vol. 17, Aug. 1999, pp. 751–752.*
Flanagan, W.M. et al. Nature Biotechnology, vol. 17, Jan. 1999, pp. 48–52.*
Crooke, S.T. Chapter 1, Basic Principles of Antisense Therapeutics in Antisense Research And Application, (ed. by Stanley T. Crooke), Springer–Verlag, New York (Jul. 1998).*
Gura, T. Science, vol. 278, Nov. 1997, pp. 1041–1042, Nov. 1997.*
Milligan, J.F. et al. Journal of Medicinal Chemistry, vol. 36, No. 14, Jul. 9, 1993, pp. 1923–1937.*
Cohen and Hogan, "The New Genetic Materials," *Scientific American*, pp. 76–82, 1994.
Crooke and Bennett, "Progress in Antisense Oligonucleotide Therapeutics," *Annu. Rev. Pharmacol. Toxicol.*, 36:107–29, 1996.
Olson et al., "Angiogenin antagonists prevent tumor growth in vivo," *Proc. Natl. Acad. Sci. U.S.A.*, 92:442–446, 1995.
Olson et al., "A Monoclonal Antibody to Human Angiogenin Suppresses Tumor Growth in Athymic Mice," *Cancer Research*, 54:4576–4579, 1994.
Wickstrom, "Antisense DNA Therapeutics, Neutral Analogs and Their Stereochemistry," *Gene Regulation: Biology of Antisense RNA and DNA*, pp. 119–132, 1992.
Zhang et al., "Pharmacokinetics of an anti–human immunodeficiency phosphorothioate oligodeoxynucleotide phosphorothioate (GEM 91) in HIV–infected subjects," *Clinical Pharmacology & Therapeutics*, 58(1):44–53, 1995.
Zon, "History of Antisense Drug Discovery," *Antisense Research and Applications*, chapt. 1, pp. 1–5, CRC Press, Inc., editors: Crooke and Lebleu, 1993.

* cited by examiner

Primary Examiner—John L. LeGuyader
Assistant Examiner—Mark L. Shibuya
(74) Attorney, Agent, or Firm—Banner & Witcoff, Ltd.

(57) ABSTRACT

Disclosed are oligonucleotide compounds that inhibit the expression of angiogenin when administered to a mammal. Also disclosed are methods and pharmaceutical compositions for inhibiting the expression of angiogenin useful in therapy or diagnosis.

8 Claims, 21 Drawing Sheets

```
-1696                                                                      TGTTTGCATTAAGTTC
-1680  ATAGATTATAATTTGTAATGAATCAACACCAAATGCAAATTAGAAAGAGAGCCCACTTTGCTCACCAGTCACGTCTTC
-1600  CCATGTAACCATAGAACGTTGGGGTCCTGTGTCTTTCTAGATCCACAGTCTTGCTCTCAGAACAGGCTAGCCACACCA
-1520  GGCCTAGTGCCAGGACCCATGGCCTTTTTTTAAGCTCAGACTCCCTTCTGTGAACAGCAATATCCCCACAACTTGTACAA
-1440  CATTGGTGCTTCCTGCAAGGCTACAGAACTATTTGATACGAAAAATGTTCATTGACTTACACAAGAGAAGCACAAAAT
-1360  AAAAAATTAATAATTAATGTCTTTGAAAATGTACCATTTATTTTTACATTTGGGGTCATAAGAATTGTATTACAC
-1280  TTAAGAATGCAATACAATTGAAGATCAGATTTTCTCCCTTGTGAGAATTTCTCAGTATGTGTGATGACTACCAAGAA
-1200  ATCATAGCCAGTCATAAATTCAGTGAGTTACTCATAAACGAACAAGAACCACCTACTTCTTGGGGAGGTAGGTCTGCTTC
-1120  CCTTCAACTCAGGATACAACTGCTTTCAACTGCTTCTTCACATTAGCTGACTAATTAGCTAGAAGCCTGTCGTAAACAA
-1040  TTTTATGGTTGACTCCTCCCTGGGCTCAGGGTTCCCTAGAACAGAGAGTCCCCAAATCCCGGTCTGTGGCCTGTCCGC
-960   CTAAGCTCTGCCTCCTGCCAGATCAGCAGGCAGCATTAGATTCTCATAGGAGCTGGACGCCTATTGTGAACTGCGCATGT
-880   GCGGGATTCCAGATTGTGCACTCTTTATGAGAATCTAACTAATGCTTGATGATCTATCTGAACCAGAACAATTCATCCTG
-800   AAACCATCCCCCACCAATCCATAGAGAAATACTGTCTTCCCAAAAATGATCCCTGGTGCCAAAAATGTTAGAGACCACTCC
-720   CCTAAAACTCTCTTCTTCTAGCTCTCACCTCCCCTGTATTACTATCTCATTGAAGCCCCCATCTTTTCCCATG
-640   GATGCCTCATTCCTATTAGGGAGGCATTTTTTATTTTGTTTTTATTTTTGTATTTTTAGTAGAGACGGGGTTCACCG
-560   CAAGGCTGGAGTGCAGTGGGCGCCATCTCGGCTCACTGCAAGCTCCGCCTCCCGGGTTCACGCCATTCTCCTGCCTCAGCC
-480   TCCCAAGTAGCTGGGACTACAGGCGCCCGCCACTACGCCCGGCTAATTTTTGTATTTTTAGTAGAGACGGGGTTTCACCG
```

Fig. 1A

```
-400   TGGTAGCCAGGATGGTCTCTCGATCTCCCTGACCTCGTGATCCGCCCGCCTTGGCCTCCCAAAGTGCTGTGGGATTACAGGCGTG
-320   AGACCCGCGCCCGGCCGTCATTTGGTATGTCTTAAGTGCCTCAGGACCTAGCACAGTCCCCTGGTACCCAGTAGAGACCTA
-240   TGTAAATGTTCGTTATTCAATAATAAATACATGAATTAAAGAGTGAGAGTGGATTTTGTAATGTTACGACTGATAGAGAAA
-160   TACTCAGTGATTCTAAGGGATGGGGGAAGAACGGTTGGAGCTAGAGGTTGTGCTCAGGAAACTATTAAATAGACGTTCCGC
-80    AGGAAGGGATTGACGAAGTGTGAGGTTAATGAGGAAGGGAAAATAGAATATAAAATTGGTGGTGGAAAGATCTGATTC
 1     ATGATGCCGTGTCAGAGAGCAAAGCTCCCTGTCCTCCTTTTGGCCTAATTGGTGATGCTGTTCTTGGGTCTACCACACCTCCT
                                                                      -24              -20
                    ⇒  Met Val Met Gly Leu Gly Val Leu Leu Leu Val Phe
+81    TTTGCCCTCCGCAGGAGCCTGTGTTGGAAGAG ATG GTG ATG GGC CTG GGC GTT TTG TTG GTC TTC
                                       -1  +1
       Val Leu Gly Leu Gly Leu Thr Pro Pro Thr Leu Ala Gln Asp Asn Ser Arg Tyr Thr His
+144   GTG CTG GGT CTG GGT CTG ACC CCA CCG ACC CTG GCT CAG GAT AAC TCC AGG TAC ACA CAC
                  -10                                                        20
       Phe Leu Thr Gln His Tyr Asp Ala Lys Pro Gln Gly Arg Asp Asp Arg Tyr Cys Glu Ser
+204   TTC CTG ACC CAG CAC TAT GAT GCC AAA CCA CAG GGC CGG GAT GAC AGA TAC TGT GAA AGC
                   10
```

Fig. 1B

```
                         30                              40
       Ile Met Arg Arg Arg Gly Leu Thr Ser Pro Cys Lys Asp Ile Asn Thr Phe Ile His Gly
+264   ATC ATG AGG AGA CGG GGC CTG ACC TCA CCC TGC AAA GAC ATC AAC ACA TTT ATT CAT GGC 50                              60
       Asn Lys Arg Ser Ile Lys Ala Ile Cys Glu Asn Lys Asn Gly Asn Pro His Arg Glu Asn
+324   AAC AAG CGC AGC ATC AAG GCC ATC TGT GAA AAC AAG AAT GGA AAC CCT CAC AGA GAA AAC 70                              80
       Leu Arg Ile Ser Lys Ser Ser Phe Gln Val Thr Thr Cys Lys Leu His Gly Gly Ser Pro
+384   CTA AGA ATA AGC AAG TCT TCT TTC CAG GTC ACC ACT TGC AAG CTA CAT GGA GGT TCC CCC 90                              100
       Trp Pro Cys Gln Tyr Arg Ala Thr Ala Gly Phe Arg Asn Val Val Val Ala Cys Glu
+444   TGG CCT CCA TGC CAG TAC CGA GCC ACA GCG GGG TTC AGA AAC GTT GTT GTT GCT TGT GAA 110                             120         123
       Asn Gly Leu Pro Val His Leu Asp Gln Ser Ile Phe Arg Arg Pro Stop
+504   AAT GGC TTA CCT GTC CAC TTG GAT CAG TCA ATT TTC CGT CGT CCG TAA

+552   CCAGCGGGCCCCTGGTCAAGTGCTGGCCTCTGCTGTCCTGCCTTCCATTCCCCCTCTGCA

+612   CCCAGAACAGTGGTGGCAACATTCATTGCCAAGGGCCCAAAGAAAGAGCTACCTGGACCTTTTGTTTCTGTTTGACAAC
                                                    ⇒
+692   ATGTTTAATAAATAAAAAATGTCTTGATATCAGTAAGAATCAGAGTCTTCTCACTGATTCTGGGCATATTGATCTTTCCCC

+782   CATTTTCTCTACTTGGCTGCTCCCTGAGAGGACTGCATAGAGATAGAAATGCCTTTTTCTTTCTTTCGTTTTTTTTT
```

Fig. 1C

+862  TTTTTTTTTGAGATGGAGTCTCACTCTGTCGCCCAGGCTTAAGTGCAATGCACAATCTCGGCTCACTGCAACCTCT
+942  CTCCTGGGTTCAAGTGATTCTCCTGCCTCAGCCTCCCAAATAGCCTGAGATTACAGGCATGCACCACCACCTGCTAAT
+1022 TTTTGTGTTTTTAGTAGACAGGGTTCACCGTTTGGCCAGTTGGTCTTGAACTCCTGACCTCGGGAGATCCGCCCA
+1102 CCTTGGCCTCTCTTTGTGCTGGGATTACAGGCATGAGCCGGGCCACTTTTCCTTATCAGTCAGTTTTACA
+1182 AGTCATTAGGGAGGTAGACTTTACCTCTCTGTGAAGGAAAGTATGGTATGTTGATCTACAGAGAGATGGAAAAATTCC
+1262 AGGGCTCGTAGCTACTAAGCAGAATTTCCAAGATAGGCAAATTGTTTTTTCTGTCAAATAATAAGCTAATATTACTTCTA
+1342 CAAATATGAGACCTTGGAGAGAAGTTTCCAAGGACCAAGTACCAACATACCAACAGATTATTATAGTTTCTCTCACTCTT
+1422 ACACACACACACACATATACACATATGTAATCCAGCATGAATAACCAAAATTCATTCAGGGTAGCCACCTTTGTCTTA
+1502 ATCGAGAGATAATTTGATGTTGAATGCTCCCAGATATTCTCTTGTCATGGTTATTTTATATAAAATTCAAAA
+1582 ACCAATTACATTATTCCTCGTAATCTTTACTTTATCAACTAATGTCTGCCAAGTGTGATGTTTTGGGAAGTTATAG
+1662 AAGATTCCGGCCAGGCGCTTATCTCACGCTTGTAATCCAGCACTTTGGGAAGCTGAGGCGGACAGATCACGAGGTCAAGA
+1742 GATCAAGACCATCCTGGACAACATGGTGAAACCTTGTCTCTACTAAAATGTGAAAATAGCTGGGCGTGGTGGCACACA
+1822 CCTATAGTCCCAGCTACTCGGGAGGCTGAGGCAGGAGAATCGCTTGAACCTAGGAGGCGGAGGTTGCACTGAGCCGAGAT
+1902 CACGCCACTGCACTCCAGCCTGGGCGACAGAGCGAGACTCCATCTCAAAAAAAAAAAAAGAAAGATCCCAGTTTATC
+1982 CCAGTTTATCCCTTATTCTTCCTCAATTCTCAAGATTTGTTTTTAAGTTAACATAACTTAGGTTAACACACTCTTTGTAA
+2062 AATACACTGTTCAATCTACAGACTCAGTGGTTAGCTTCCTGTTAACTAATTTCTGTTGACAGGTACTTGGATATTTATT

Fig. 1D

```
+2142  TAGAAAGTGGTTGCCAATAAATTAGTTATAAGTCGCCAGTTTCACTGCCTTGTGAACACATAATTATTGTGGTCTCAGTA
+2222  TTCCCTATGTGGCTTCTCCTGCTCCCTGGTATTGCCCTGAAATGGGCCAAAAGCCCGTGGCTCCCCAATGCTCAGGTTATA
+2302  GAACATTGTCCAGGTACCACCTAGGAGAGCCCAGCCTCACTGAAAGTATTCAAATTTAGGAATGGGTTTGAGAAGTAGGT
+2382  AGCTGGTATGTGCTTAGCACAAGAATCTCTCTCCTTGGGTTAGTCTGTGTTTCAAAACTGAAAACACTGTCATTCCTTAAG
+2462  AAAATAGGAAAAAGTATTCCAAACCCTCTGTCACTAGAAAAATTTGCCATATTACCAAATCTCAAAAACCTCTCAGGAAATG
+2542  AGAAAGTCCCAGTTTCTCGGTAAACTATTTGGGCCCTTTTCTCAAGTTCTCCTTCCAGTGCTATTCCTTGAGGTGAGGCA
+2622  AAGTTACTCAAGATCATCGCTGCCACTCAAGGCCTTGATAGGGCAAGTGAAAGGCATGGACCATTATTATATTGATCACA
+2702  GCATAAGCTGTGAAAACCCACATCTTCTCCAAACATCTGCTTGGAGCATTATCATCGCATAGTTGCTCTGGTGTTCAGG
+2782  GAAATCGCTGTGTTTCATAGGAAATCACATGGCAGTGGGATGGGAGTGTTCCTGACCTGCCGATGGTACTGGCACCTGAGC
+2862  AAGCATTCCTAGTCCTTTTGGTCTGGGCCTCTGTTCTATCACAACCACAAGCTGTTTAAAATAAAAACGTCAAGTCAC
+2942  AGGCAGGTCATTTTATCCTGCGTGAATCAATTGAAG
```

Fig. 1E

ANTISENSE INHIBITION OF ANGIOGENIN EXPRESSION

This application claims benefit of U.S. Provisional Application Ser. No. 60/041,182 filed Mar. 21, 1997 hereby incorporated by reference in its entirety.

This application was funded in part by National Institutes of Health/National Cancer Institute grant no. RO1 CA60046.

BACKGROUND OF THE INVENTION

1. Field of the Invention

Embodiments of the present invention relate in general to compositions and methods for inhibiting the expression of the angiogenin gene thereby reducing the effects of angiogenin. Embodiments of the present invention also relate to inhibition of angiogenin gene expression by antisense technologies including, but not limited to, the use of antisense oligodeoxynucleotides and their derivatives. Embodiments of the present invention are further directed to compositions and methods for detecting the angiogenin gene, as well as the detection and diagnosis of abnormal expression of the angiogenin gene in cells and tissues. Embodiments of the present invention are also directed to methods for inhibiting metastasis of cells, such as human tumor cells. Furthermore, this invention is directed to treatment of conditions associated with abnormal angiogenesis, including cancer.

2. Description of Related Art

Angiogenin is a potent inducer of angiogenesis [Fett, J. W., Strydom, D. J., Lobb, R. R., Alderman, E. M., Bethune, J. L., Riordan, J F., and Vallee, B. L. (1985) *Biochemistry* 24, 5480–5486], a complex process of blood vessel formation that consists of several separate but interconnected steps at the cellular and biochemical level: (i) activation of endothelial cells by the action of an angiogenic stimulus, (ii) adhesion and invasion of activated endothelial cells into the surrounding tissues and migration toward the source of the angiogenic stimulus, and (iii) proliferation and differentiation of endothelial cells to form a new microvasculature [Folkman, J., and Shing, Y. (1992) *J. Biol. Chem.* 267, 10931–10934; Moscatelli, D., and Rifikin, D. B. (1988) *Biochim. Biophys. Acta* 948,67–85]. Angiogenin has been demonstrated to induce most of the individual events in the process of angiogenesis including binding to endothelial cells [Badet, J., Soncin, F. Guitton, J. D., Lamare, O., Cartwright, T., and Barritault, D. (1989) *Proc. NatL. Acad. Sci. U.S.A.* 86, 8427–8431], stimulating second messengers [Bicknell, R., and Vallee, B. L. (1988) *Proc. Natl. Acad. Sci. U.S.A.* 85, 5961–5965], mediating cell adhesion [Soncin, F. (1992) *Proc. Natl. Acad. Sci. U.S.A.* 89, 2232–2236], activating cell-associated proteases [Hu, G-F., and Riordan, J. F. (1993) *Biochem. Biophys. Res. Commun.* 197, 682–687], inducing cell invasion [Hu, G-F., Riordan, J. F., and Vallee, B. L. (1994) *Proc. Natl. Acad. Sci. U.S.A.* 91, 12096–12100], inducing proliferation of endothelial cells [Hu, G-F., Riordan, J. F., and Vallee, B. L. (1997) *Proc. Natl. Acad. Sci. U.S.A.* 94, 2204–2209] and organizing the formation of tubular structures from the cultured endothelial cells [Jimi, S-I., Ito, K-I, Kohno, K., Ono, M., Kuwano, M., Itagaki, Y., and Isikawa, H. (1995) *Biochem. Biophys. Res. Commun.* 211, 476–483]. Angiogenin has also been shown to undergo nuclear translocation in endothelial cells via receptor-mediated endocytosis [Moroianu, J., and Riordan, J. F. (1994) *Proc. Natl. Acad. Sci. U.S.A.* 91, 1677–1681] and nuclear localization sequence-assisted nuclear import [Moroianu, J., and Riordan, J. F. (1994) *Biochem. Biophys. Res. Commun.* 203, 1765–1772].

Although originally isolated from medium conditioned by human colon cancer cells (Fett et al., 1985, supra) and subsequently shown to be produced by several other histologic types of human tumors [Rybak, S. M., Fett, J. W., Yao, Q-Z., and Vallee, B. L. (1987) *Biochem. Biophys. Res. Commun.* 146, 1240–1248; Olson, K. A., Fett, J. W., French, T. C., Key, M. E., and Vallee, B. L. (1995) *Proc. Natl. Acad. Sci. U.S.A.* 92, 442–446], angiogenin also is a constituent of human plasma and normally circulates at a concentration of 250 to 360 ng/ml [Shimoyama, S., Gansauge, F., Gansauge, S., Negri, G., Oohara, T., and Beger, H. G. (1996) *Cancer Res.* 56, 2703–2706; Blaser, J., Triebl, S., Kopp, C., and Tschesche, H. (1993) *Eur. J. Clin. Chem. Clin. Biochem.* 31, 513–516].

While angiogenesis is a tightly controlled process under usual physiological conditions, abnormal angiogenesis can have devastating consequences as in pathological conditions such as arthritis, diabetic retinopathy and tumor growth. It is now well-established that the growth of virtually all solid tumors is angiogenesis dependent [Folkman, J. (1989) *J. Natl. Cancer Inst.* 82, 4–6]. Angiogenesis is also a prerequisite for the development of metastasis since it provides the means whereby tumor cells disseminate from the original primary tumor and establish at distant sites [Mahadevan, V., and Hart, I. R. (1990) Rev. Oncol. 3, 97–103; Blood C. H., and Zetter B. R. (1990) *Biochim. Biophys. Acta* 1032, 89–118]. Therefore, interference with the process of tumor-induced angiogenesis should be an effective therapy for both primary and metastatic cancers.

Several inhibitors of the functions of angiogenin have been developed. These include: (i) monoclonal antibodies (mAbs) [Fett, J. W., Olson, K. A., and Rybak, S. M. (1994) *Biochemistry* 33, 5421–5427], (ii) an angiogenin-binding protein [Hu, G-F, Chang, S-I, Riordan J. F., and Vallee, B. L. (1991) *Proc. Natl. Acad. Sci. U.S.A.* 88, 2227–2231; Hu, G-F., Strydom, D. J., Fett, J. W., Riordan, J. F., and Vallee B. L. (1993) *Proc. Natl. Acad. Sci. U.S.A.* 90,1217–1221; Moroianu, J., Fett, J. W., Riordan, J. F., and Vallee B. L. (1993) *Proc. Natl. Acad. Sci. U.S.A.* 90, 3815–3819], (iii) the placental ribonuclease inhibitor (PRI) [Shapiro, R., and Vallee, B. L. (1987) *Proc. Natl. Acad. Sci. U.S.A.* 84, 2238–2241], (iv) peptides synthesized based on the C-terminal sequence of angiogenin [Rybak, S. M., Auld, D. S., St. Clair, D. K., Yao, Q-Z., and Fett, J. W. (1989) *Biochem. Biophys. Res. Commun.* 162, 535–543], and (v) inhibitory site-directed mutants of angiogenin [Shapiro, R., and Vallee, B. L. (1989) *Biochemistry* 28, 7401–7408]. All inhibit angiogenin's activities but are not directly cytotoxic to human tumor cells grown in tissue culture.

mAbs or the angiogenin-binding protein when administered locally into xenografts of human tumor cells that were injected subcutaneously (s.c.) into athymic mice are able to delay or, remarkedly, completely prevent the appearance of colon, lung and fibrosarcoma tumors in these animals [Olson et al., 1995, supra, Olson, K. A., French, T. C., Vallee, B. L., and Fett, J. W. (1994) *Cancer Res.* 54, 4576–4579]. Histological examination revealed that the mechanism of tumor growth inhibition was via an anti-angiogenesis mechanism (Olson et al., 1995, supra). Thus, the inactivation of tumor-produced angiogenin or inhibition of expression of the angiogenin gene by tumor cells promise to be a powerful means of managing cancer, either alone or in combination with more conventional therapies (i.e., chemotherapy, radiotherapy, immunotherapy, etc.).

Expression of specific genes may be suppressed by oligonucleotides having a nucleotide sequence complementary to the mRNA transcript of the target gene thereby selectively impeding translation and has been termed an "antisense" methodology. In addition, "antigene" or "triplex" methodologies may also suppress expression of genes by using an oligonucleotide which is complementary to a selected site of double stranded DNA thereby forming a triple-stranded complex to selectively inhibit transcription of the gene. Both "antisense" and "antigene" methodologies find utility as molecular tools for genetic analysis. Antisense oligonucleotides have been extensively used to inhibit gene expression in normal and abnormal cells in studies of the function of various cell proteins. Major advances have been made in the development of antisense or antigene reagents for the treatment of disease states in animals and humans ["Antisense Therapeutics" Agrawal, S. (ed.), Humana Press, 1996; Crooke, S. T., and Bennett, C. F. (1996) *Annu. Rev. Pharmacol. Toxicol.* 36, 107–129; "Prospects for the Therapeutic Use of Antigene Oligonucleotides", Maher, L. J. (1996) *Cancer Investigation* 14(1), 66–82 each hereby incorporated by reference in its entirety].

As therapeutics, oligonucleotides possess two major requirements for successful drug design—specificity and affinity. These are achieved by selectively targeting particular DNA or RNA sequences exploiting Watson-Crick base pairing with resulting interference of protein production whether through inhibition of gene transcription or translation of mRNA. This approach allows for rapid identification of lead compounds based on knowledge of a relevant gene target species. Recently, improvements have been made in increasing both the stability and affinity of these compounds. Phosphorothioate analogs of oligodeoxynucleotides (ODNs), in which nonbridging phosphoryl oxygens in the backbone of DNA are substituted with sulfur, abbreviated [S]ODNs, are substantially more stable than their native phosphodiester counterparts, while other derivatives, such as those alkylated on sugar oxygen groups, show enhanced target affinity. [S]ODNs possess good biological activity, pharmacology, pharmacokinetics and safety in vivo (Agrawal, 1996, supra, and references therein) and have been used successfully for anti-tumor therapy in animal models (Crooke and Bennett, 1996, supra). Antisense reagents are now in clinical trials for treatment of cancers and viral infections (Agrawal, 1996, supra). Successful inhibition of specific gene function has been achieved by targeting various sites on specific mRNA sequences that include the AUG translational initiation codon, 5'-transcriptional start site, 3'-termination codon and sequences in both the 5'- and 3'-untranslated regions. Experience to date has indicated that success has been achieved by targeting these and other regions.

As examples, U.S. Pat. No. 5,098,890 is directed to antisense oligonucleotides complementary to the c-myb oncogene and antisense oligonucleotide therapies for certain cancerous conditions. U.S. Pat. No. 5,135,917 provides antisense oligonucleotides that inhibit human interleukin-1 receptor expression. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 is directed to a mixed linkage oligonucleotide phosphorothioates complementary to an oncogene. U.S. Pat. No. 5,276,019 and U.S. Pat. No. 5,264,423 are directed to phosphorothioate oligonucleotide analogs used to prevent replication of foreign nucleic acids in cells. The nucleic acid sequence of the entire angiogenin gene including the 5'- and 3'-flanking regions has been determined [Kurachi, K., Davie, E. W., Strydom, D. J. Riordan, J. F. and Vallee, B. L. (1985) *Biochemistry* 24, 5494–5499 hereby incorporated by reference in its entirety]. The native DNA segment coding for angiogenin, as all such mammalian DNA strands, has two strands; a sense strand and an antisense strand held together by hydrogen bonding. The messenger RNA coding for angiogenin has the same nucleotide sequence as the sense strand except that the DNA thymidine is replaced by uridine. Thus, synthetic antisense nucleotide sequences should bind with the DNA and RNA coding for angiogenin.

However, it is unknown whether antisense reagents will in fact be effective for inhibition of angiogenin expression. To date, no oligonucleotide antisense reagents have been designed or demonstrated to be useful in the inhibition of the expression of angiogenin. Accordingly, a need exists to discover oligonucleotide antisense reagents which can prove useful in modulating or inhibiting the expression of angiogenin and to further discover methods by which such oligonucleotide antisense reagents can be used in methods of diagnosis and treatment.

SUMMARY OF THE INVENTION

Embodiments of the present invention are based on the discovery of oligonucleotide reagents capable of targeting nucleic acid sequences encoding angiogenin in a manner to inhibit (i.e., reduce, eliminate or otherwise interfere with) the expression of angiogenin. Each oligonucleotide, or analog thereof, has a nucleotide or base sequence which is complementary, i.e. capable of hybridizing with or binding to, at least a target portion of the nucleic acid encoding angiogenin, i.e. the angiogenin gene DNA or RNA, which has significance in expressing angiogenin. In accordance with one aspect of the present invention, targeted RNA or DNA, or cells containing it are contacted with oligonucleotide or analogs thereof which are configured to bind to the RNA or DNA in a manner to inhibit the expression of angiogenin whether by interfering with gene transcription as in an antigene strategy or by interfering with translation of MRNA as in an antisense strategy.

Embodiments of the present invention are further directed to methods for inhibiting the expression of angiogenin in a mammal by administering to or otherwise treating the mammal with an effective amount of an oligonucleotide or analog thereof having a base sequence complementary to a target portion of a nucleic acid encoding angiogenin so as to inhibit the expression of angiogenin. Embodiments of the present invention are also directed to methods for reducing size of tumors associated with angiogenesis in a mammal comprising administering to the mammal an effective amount of an oligonucleotide or analog thereof having a base sequence complementary to a target portion of a nucleic acid encoding angiogenin so as to reduce tumor size. Embodiments of the present invention are further directed to methods for decreasing production of angiogenin in a mammal comprising administering to the mammal an effective amount of an oligonucleotide or analog thereof having a base sequence complementary to a target portion of a nucleic acid encoding angiogenin so as to decrease production of angiogenin. Embodiments of the present invention are still further directed to methods for inhibiting metastasis of tumor cells in a mammal comprising administering to the mammal an effective amount of an oligonucleotide or analog thereof having a base sequence complementary to a target portion of a nucleic acid encoding angiogenin so as to inhibit metastasis of tumor cells. Embodiments of the present invention are even still further directed to methods for inhibiting the establishment of tumor cells in a mammal comprising administering to the mammal an effective amount of an oligonucleotide or analog thereof having a base sequence complementary to a target portion of a nucleic acid encoding angiogenin so as to inhibit establishment of tumor cells. Embodiments of the present invention are even still further directed to methods for inhibiting growth of tumors associated with angiogenesis in a mammal comprising administering to the mammal an effective amount of an oligonucleotide or analog thereof having a base sequence complementary to a target portion of a nucleic acid encoding angiogenin so as to inhibit tumor growth. The oligonucleotides, analogs thereof and methods described herein are therefore useful in methods of therapeutically treating a mammal, including a human, afflicted with pathological conditions associated with abnormal or unwanted angiogenesis, including cancer.

As an alternate embodiment of the present invention, labeled oligonucleotides may also be useful for diagnosing conditions associated with abnormal angiogenin expression since the labeled oligonucleotides of the present invention can also bind to the angiogenin gene, DNA or RNA and then can be detected and/or measured. Alternate embodiments of the present invention include methods detecting the presence of angiogenin in a sample comprising contacting the sample with a labeled oligonucleotide or analog thereof having a base sequence complementary to a target portion of a nucleic acid encoding angiogenin, allowing the labeled oligonucleotide or analog thereof to bind to the target portion of the nucleic acid encoding angiogenin, and detecting the labeled oligonucleotide or analog thereof. A further alternate embodiment of the present invention includes methods for detecting the presence of angiogenin in a mammal comprising administering to the mammal a labeled oligonucleotide or analog thereof having a base sequence complementary to a target portion of a nucleic acid encoding angiogenin, allowing the labeled oligonucleotide or analog thereof to bind to the target portion of the nucleic acid encoding angiogenin, and detecting the labeled oligonucleotide or analog thereof. A still further alternate embodiment of the present invention includes methods for diagnosing conditions associated with abnormal angiogenesis in a mammal comprising administering to the mammal a labeled oligonucleotide or analog thereof having a base sequence complementary to a target portion of a nucleic acid encoding angiogenin, allowing the labeled oligonucleotide or analog thereof to bind to the target portion of the nucleic acid encoding angiogenin, detecting the labeled oligonucleotide or analog thereof, measuring the labeled oligonucleotide or analog thereof, and determining the abnormal condition based on the detecting and measuring of the labeled oligonucleotide or analog thereof.

These and other objects, features and advantages of the present invention will become apparent by reference to the remaining portions of the specification and the attached drawings.

BRIEF DESCRIPTION OF DRAWINGS

In the course of the detailed description of certain preferred embodiments to follow, reference will be made to the attached drawings, in which, FIG. 1 (SEQ ID NO.: 1) depicts the nucleic acid sequence of the entire human angiogenin gene including the cDNA sequence as identified by arrows.

DETAILED DESCRIPTION OF CERTAIN PREFERRED EMBODIMENTS

Figures 2A, 2B:
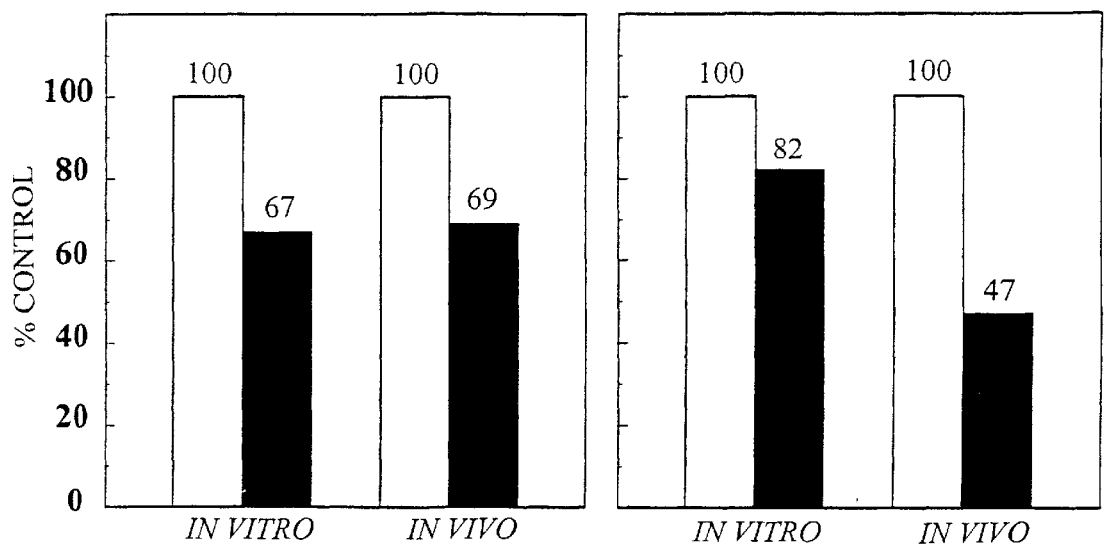
FIGS. 2A and 2B are graphs depicting the inhibition by angiogenin antisense [S]ODN JF2S (SEQ ID NO.: 4) of angiogenin expression by PC-3 tumor cells in vitro and their subsequent growth in vivo.

The principles of the present invention may be advantageously applied to produce novel oligonucleotides or analogs thereof which bind to or otherwise target nucleic acids encoding angiogenin. The oligonucleotides or analogs thereof interfere with the normal function of the nucleic acids and otherwise inhibit the transcription, replication or translation associated with the expression of angiogenin.

Angiogenesis is prominent in solid tumor formation and metastasis. Angiogenic factors have been found associated with several solid tumors such as rhabdomyosarcomas, retinoblastoma, Ewing, sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. The present invention is directed towards prevention of angiogenesis in the treatment of these and other angiogenesis dependent tumors and the resultant damage to the mammal due to the presence of the tumor.

Angiogenesis is also associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that gives rise to leukemia-like tumnors.

Angiogenesis is important in two stages of tumor metastasis. The first stage where angiogenesis stimulation is important is in the vascularization of the tumor which allows cells to enter the blood stream and to circulate throughout the body. After the tumor cells have left the primary site, and have settled into the secondary, metastasis site, angiogenesis must occur before the new tumor can grow and expand. Therefore, embodiments of the present invention are directed to the inhibition of angiogenesis as a treatment for the prevention of metastasis of tumors and containment of the neoplastic growth at the primary site.

Examples of diseases mediated by angiogenesis are disclosed in the prior art such as U.S. Pat. No. 5,712,291 and include ocular neovascular disease as well as the other diseases to follow. Ocular neovascular disease is characterized by invasion of new blood vessels into the structure of the eye such as the retina or cornea. It is the most common cause of blindness and is involved in approximately twenty eye diseases. In age-related macular degeneration, the associated visual problems are caused by an ingrowth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, mycobacteria infections, lipid degeneration, chemical burns, bacterial ulcers, fungal ulcers, Herpes simples infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegener's sarcoidosis, Scleritis, Steven Johnson's disease, periphigoid radical keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/ vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering from arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed with the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumor of blood or lymph vessels. The angiomas are found in the skin and mucous membranes, often accompanied by epistaxis (nosebleeds) or gastrointestinal bleeding sometimes with pulmonary or hepatic arteriovenous fistula.

Embodiments of the present invention further include treatment of the above disease states through the inhibition of angiogenesis The relationship between an oligonucleotide and its complementary nucleic acid target to which it hybridizes is commonly referred to as "antisense" if the complementary nucleic acid target is single stranded or "antigene" or "triplex" if the complementary nucleic acid target is double stranded. It is to be understood that the oligonucleotides and methods of the present invention described herein are useful in both antisense or antigene approaches. Accordingly, those terms are used interchangeably herein.

In accordance with the teachings of the present invention, the oligonucleotide employed in the methods of the present invention will generally have a sequence that is complementary to the sequence of the target nucleic acid whether that be in the form of single stranded RNA or DNA or double stranded DNA. "Targeting" an oligonucleotide to a nucleic acid sequence of the angiogenin gene includes determining a site or sites within the nucleic acid sequence for the oligonucleotide interaction to occur such that the inhibition of the expression of angiogenin will result. "Inhibition of the expression of angiogenin" is herein defined as that phrase is normally understood and to also include the elimination of, prevention of, reduction of or other interference with the expression of angiogenin occurring prior to or in the absence of the interaction between the oligonucleotide and the nucleic acid sequence of the angiogenin gene. "Inhibition" itself is herein defined as the elimination of, prevention of, reduction of or other interference with the particular mechanism being interfered with. Once the desired target site or sites have been identified anywhere along the entire nucleic acid sequence of the angiogenin gene, one or more oligonucleotides are chosen which are sufficiently complementary to the target, i.e. hybridize sufficiently well and with sufficient specificity, to inhibit the expression of angiogenin.

The terms "hybridization" or "to bind" as used herein means hydrogen bonding, also known as Watson-Crick base pairing, between complementary bases (i.e. purines or pyrimidines), usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. The letters A, G, C, T, and U respectively indicate nucleotides in which the nucleoside is adenosine, guanosine, cytidine, thymidine, and uridine. As used herein, oligonucleotides that are antisense to the target angiogenin nucleic acid sense strand are oligonucleotides which have a nucleoside sequence complementary to the sense strand. Table 1 shows the four possible sense strand bases and their complements present in an antisense compound.

TABLE 1

| Sense | Antisense |
| --- | --- |
| Adenine | Thymine |
| Quanine | Cytosine |
| Cytosine | Guanine |
| Thymine | Adenine |

"Specifically hybridizable" and "complementary" are terms which are used to indicate a sufficient degree of complementarity such that stable and specific binding occurs between the target nucleic acid and the oligonucleotide. It is to be understood that an oligonucleotide need not be 100% complementary to its target nucleic acid to be specifically hybridizable, i.e. it may lack one or more complements for certain nucleotides in the targeted nucleic acid sequence. An oligonucleotide is specifically hybridizable when binding of the oligonucleotide to the target nucleic acid inhibits the normal function of the target nucleic acid to cause a loss of utility whether of transcription or translation, and there is a sufficient degree of complementarity to avoid non-specific binding of the oligonucleotide to non-target sequences under conditions in which specific binding is desired, i.e. under physiological conditions in the case of in vivo assays or therapeutic treatment, or in the case of in vitro assays, under conditions in which the assays are conducted. Accordingly, absolute complementarity is not required in the practice of the present invention. In general, any oligonucleotide having sufficient complementarity to form a stable duplex with the target single stranded RNA or DNA or a stable triplex with the target double stranded DNA is considered to be suitable. Since stable duplex or triplex formation depends on the sequence and length of the hybridizing oligonucleotide and the degree of complementarity between the antisense oligonucleotide and the target sequence, the system can tolerate less fidelity (complementarity) when longer oligonucleotides are used. In short, any interaction or binding of an oligonucleotide or oligonucleotide analog with a target nucleic acid encoding angiogenin is believed to have the potential to inhibit the expression of angiogenin.

In the context of this invention, the term "oligonucleotide" refers to a plurality of joined nucleotide units formed from naturally-occurring bases and ribofuranosyl groups joined by native phosphodiester bonds. This term effectively refers to naturally-occurring species or synthetic species formed from naturally-occurring subunits and includes both oligomers of ribonucleotide i.e., oligoribonucleotides, and oligomers of deoxyribonucleotide i.e, oligodeoxyribonucleotides (also referred to herein as "oligodeoxynucleotides"). As used herein, unless otherwise indicated, the term "oligonucleotide" also includes oligomers which may be large enough to be termed "polynucleotides". As further used herein, the terms "oligonucleotide" and "oligodeoxynucleotide" include not only oligomers and polymers of the biologically significant nucleotides, i.e. nucleotides of adenine ("A"), deoxyadenine ("dA"), guanine ("G"), deoxyguaninc ("dG"), cytosine ("C") deoxycytosine ("dC"), thymine ("T") and uracil ("U"), but also oligomers and polymers hybridizable to angiogenin DNA or RNA which may contain other nucleotides.

"Oligonucleotide analog" as that term is used in coimection with this invention, refers to a compound having a modified internucleotide linkage, a modified purine or pyrimidine moiety, a modified sugar moiety, a modified 5' hydroxyl moiety, a modified 3' hydroxyl moiety or a modified 2' hydroxyl moiety. The analogs including the modified moieties function similarly to oligonucleotides in that they hybridize or otherwise bind to target nucleic acids but which have non naturally-occurring portions wherein one or more purine or pyrimidine moieties, sugar moieties or internucleotide phosphate linkages is chemically modified, for example, to improve stability and/or lipid solubility to enhance the ability of the oligonucleotides to penetrate into the region of cells where the RNA whose activity is to be modulated is located. For example, it is known that enhanced lipid solubility and/or resistance to nuclease digestion results by substituting a methyl group or sulfur atom for a phosphate oxygen in the internucleotide phosphodiester linkage.

Exemplary among these are the phosphorothioate and other sulfur containing species which are known in the art. Phosphorothioates are compounds in which one of the non-bridging oxygen atoms in the phosphate portion of the nucleotide is replaced by sulfur. These phosphorothioates are stable to cleavage by nucleases, and since they have the same number of charges as normal oligodeoxynucleotides, they have good aqueous solubility. Other modified oligonucleotides or analogs such as alkyl phosphorothioate, phosphodiester, phosphotriester, N-alkyl phosphoramidates, phosphorodithioates, alkyl phosphonates, and short chain alkyl or cycloalkyl structures may also be useful. In accordance with other preferred embodiments, one or more phosphodiester bonds are substituted with structures which are, at once, substantially non-ionic and non-chiral to produce mixed linkage oligonucleotides. Persons of ordinary skill in the art will be able to select other linkages for use in the practice of the invention.

Oligonucleotide analogs may also comprise altered base or sugar units, have charged or uncharged backbones, have additions at the ends of the oligonucleotide molecule or other modifications consistent with the spirit of this invention. Such analogs are best described as being functionally interchangeable with natural oligonucleotides (or synthesized oligonucleotides along natural lines), but which have one or more differences from natural structure. All such analogs are comprehended by this invention so long as they can function effectively to bind to selected portions of nucleic acids encoding angiogenin.

In accordance with the principles of the present invention, oligonucleotides complementary to and hybridizable with any portion of nucleic acids responsible for expression of angiogenin whether human or animal are, in principle, effective for inhibiting the expression of angiogenin in the respective mammal. It is therefore to be understood that the principles of the present invention apply to all mammals, including humans, where inhibition of the expression of angiogenin is desired. For example, the nucleic acid sequence encoding mouse angiogenin is known. See Bond, M. D., and Vallee, B. L. (1990) Biochem. Biophys. Res. Commun. 171, 988–995. The nucleic acid sequence for human angiogenin is shown in FIG. 1. Accordingly, the application of the principles of the present invention not only include human uses, but animal uses as well.

Oligonucleotides according to certain embodiments of the present invention are represented by Formula I below although additional embodiments are described throughout this disclosure:

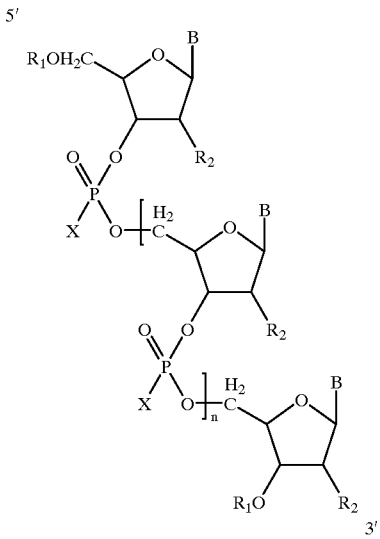

Formula I in which

X is O, S, or $C_{1-4}$ alkyl;

B is adenine, guanine, cytosine, or thymine selected such that the oligonucleotide has a complementary base sequence with a portion of the nucleic acid strand coding for angiogenin thereby inhibiting expression thereof, $R_1$ is H, $C_{1-4}$ alkyl or substituted acridine;

$R_2$ is H, OH, SH, F, $OCH_3$, OCN, or $OCH_6CH_3$; and n is 5 to 100.

Oligonucleotides within the scope of the present invention, including those represented by Formula I, include pharmaceutically acceptable salts or hydrates thereof. Oligonucleotides within the scope of the present invention optionally may include intercalating molecules or ribozyme sequences and may optionally have intervening sequences of other nucleotides or non-nucleotide molecules provided that such oligonucleotides hybridize with angiogenin DNA or RNA and inhibit its expression.

While any length oligonucleotide may be utilized in the practice of the invention, such as an oligonucleotide complementary to the entire angiogenin gene, oligonucleotides having between 5 to 100 subunits find utility and are preferred in the practice of the present invention. It is preferred that such oligonucleotides and analogs comprise at least about 5 subunits with from about 8 to 50 subunits being more preferred. As will be appreciated, a subunit is a base and sugar combination suitably bound to adjacent subunits through phosphodiester or other modified bonds as previously discussed.

Oligonucleotides shorter than 15 bases may be less specific in hybridizing to the target angiogenin mRNA, and may be more easily destroyed by enzymatic digestion. Hence, oligonucleotides having 15 or more nucleotides are preferred. Sequences longer than 18 to 25 nucleotides may be somewhat less effective in inhibiting angiogenin translation because of decreased uptake by the target cell. Thus, oligomers of 15–25 nucleotides are most preferred in the practice of the present invention, particularly oligomers of 15–18 nucleotides.

It is to be understood that oligonucleotides having a sequence complementary to any region of the angiogenin gene find utility in the present invention, however oligodeoxynucleotides complementary to a portion of (i) the "AUG" translational start site, (ii) the 5'-transcription initiation site, (iii) the 5'-"TATA" box site and , (iv) the 3'-termination site are particularly preferred. Random sequences in both the 5'-untranslated and 3'-untranslated regions are also useful target nucleic acids for designing oligonucleotides for the inhibition of the expression of angiogenin.

Oligonucleotides of the present invention, including those represented by Formula I, hybridize or otherwise bind to target nucleic acids encoding for angiogenin, the entire gene sequence of which is shown in FIG. 1. When X in Formula I is oxygen, the nucleotides are connected by phosphodiester bonds. However, oligonucleotides of the present invention include analogs which differ from native DNA in that some or all of the phosphates in the nucleotides are replaced by phosphorothioates (in the case of X being sulfur), methylphosphonates (in the case of X being $CH_3$) or other $C_{1-4}$ alkylphosphonates such as ethyl, propyl, butyl, methyl phosphonate analogs disclosed by U.S. Pat. No. 4,469,863, phosphonate modified oligodeoxynucleotides described by LaPlanche, et al. Nucleic Acid Research 14:9081 (1986) and by Stec. et al. J. Am Chem. Soc. 106:6077 (1984), phosphodiesters and phosphotriesters. These compounds are referred to herein as having a modified oligonucleotide linkage moiety. Furthermore, recent advances in the production of oligoribonucleotide analogues mean that other agents may also be used for the purposes described here, e.g. 2'-methylribonucleotides (Inoue et al. Nucleic Acids Res. 15,6131, 1987) and chimeric oligonucleotides that are composite RNA-DNA analogues (Inoue et al. FEBS Lett. 215, 327, 1987).

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with $CH_2$—NH—O—$CH_2$, $CH_2$—N($CH_3$)—O—$CH_2$, $CH_3$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. 5,034,506. In other preferred embodiments, such as the protein-nucleic acid or peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, Science 1991, 154, 1497.

The oligonucleotides of Formula I optionally may be further differentiated from native DNA by replacing one or both of the free hydroxy groups with $C_{1-4}$ alkoxy groups (in the case of $R_1$ being $C_{1-4}$ alkyl). As used herein, $C_{1-4}$ alkyl means a branched or unbranched hydrocarbon having 1 to 4 carbon atoms.

Formula I oligonucleotides may also be substituted at the 3' and/or 5' ends by $R_1$ being an intercalating agent such as a "substituted acridine" which means any acridine derivative capable of intercalating nucleotide strands such as DNA. Preferred substituted acridines are 2-methoxy-6-chloro-9-pentylaminoacridine, N-(6-chloro-2-methoxyacridinyl)-O-methoxydiisopropylaminophosphinyl-3-aminopropanol and N-(6-chloro-2-methoxyacridinyl)-O-methoxydiisopropylaminophosphiny-5-aminopentanol. Other suitable acridine derivatives are readily apparent to persons skilled in the art.

Formula I oligonucleotides may also include ribozyme sequences inserted into their nucleotide sequence. The ribozyme sequences are inserted into Formula I compounds such that they are immediately preceded by AUC, UUC, GUA, GUU, GUC, or, preferably, CUC. The ribozyme sequence is any sequence which can be inserted and causes self-cleavage of messenger RNA. The sequence CUG AUG AGU CCG UGA CGA A is preferred. Other such sequences can be prepared as described by Haseloff and Gerlach, Nature (Aug. 18, 1988) 334; 585–591.

It is generally preferred for use in some embodiments of this invention that the 2' position of the linking sugar moieties in at least some of the subunits of the oligonucleotides or oligonucleotide analogs be substituted. Thus, 2' substituents such as $R_2$ is OH, SH, $SCH_2$, $OCH_3$, F, OCN, $OCH_6$ $CH_3$, $OCH_3$ $OCH_3$, $OCH_3O(CH_2)_n$ $CH_3O(CH_2)_nNH_2$ or O $(CH_2)_nCH_3$ where n is from 1 to about 10; $C_1$ to $C_{10}$ lower alkyl, substituted lower alkyl, alkaryl or aralkyl; Cl ; Br; CN; $CF_3$; $OCF_3$; O, S, or N-alkyl; O, S, or N-alkenyl; $SOCH_3$; $SO_2CH_3$; $ONO_2$; $NO_2$; $N_3$; $NH_2$; heterocycloalkyl or alkaryl; aminoalkylamino; polyalkylamino; substituted silyl: an RNA cleaving group; a cholesteryl group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides having sugar mimetics such as cyclobutyls in place of the pentofuranosyl group are useful in the present invention. Other preferred embodiments may include at least one modified base form or "universal base" such as inosine.

Synthesis of Antisense Oligonucleotides

The oligonucleotides used in accordance with this invention may be conveniently and routinely made through the well-known technique of solid phase synthesis on automated nucleic acid synthesizers, such as the Applied Biosystems 380B DNA Synthesizer which utilizes β-cyanoethyl phosphoramidite chemistry. Alternatively, the oligonucleotides of the invention may be synthesized by any of the known chemical oligonucleotide synthesis methods. Such methods are generally described, for example in Winnacker, *From Genes to Clones: Introduction to Gene Technology*. VCH Verlagsgesellshaft mbH (H. Ibelgaufts trans. 1987).

Any other means for such synthesis may also be employed; the actual synthesis of the oligonucleotides is well within the talents of the routineer. It is also well known to use similar techniques to prepare other oligonucleotides such as phosphorothioates and alkylated derivatives. For example, Formula I oligonucleotides in which one or more X is S are prepared by published procedures which are incorporated herein by reference. Stec., W. J. et al *J. Am. Chem. Soc.* (1984) 106:6077–6079; Adams, S. P. et al. *J. Am. Chem. Soc.* (1983) 105:661; Caruthers, M. H., et al, *Genetic Engineering; Settlow*, J. Hollander. A. Eds; Plenum Press: New York (1982) 4:1 Broido, M. S. et al; *Biochem Riophys. Res. Commun.* (1984)119:663. It is also well known to use similar techniques and commercially available modified amidite and controlled pore glass (CPG) products such as biotin, fluorescein, acridine and psoralen-modified amidites and/or CPG to synthesize fluorescently labeled, biotinylated or other modified oligonucleotides.

Since the complete gene sequence of certain mamalian angiogenins are known, including human and mouse, oligonucleotides hybridizable with any portion of the gene sequence or the mRNA transcript may be prepared by the oligonucleotide synthesis methods known to those skilled in the art.

Dosage and Administration

Overall, it is preferred to administer oligonucleotides or analogs thereof to mammals suffering from the effects of abnormal angiogenesis, such as tumor growth, in either native form or suspended in a carrier medium in amounts and upon treatment schedules which are effective to therapeutically treat the mammals to reduce the effects of abnormal angiogenesis. One or more different oligonucleotides or analogs thereof targeting different sections of the nucleic acid sequence of angiogenin may be administered together in a single dose or in different doses and at different amounts and times depending upon the desired therapy. The oligonucleotides can be administered to mammals in a manner capable of getting the oligonucleotides initially into the blood stream and subsequently into cells, or alternatively in a manner so as to directly introduce the oligonucleotides into the cells or groups of cells, for example tumor cells, by such means by electroporation or by direct injection into the tumor. Oligonucleotides whose presence in cells can inhibit transcription or protein synthesis can be administered by intravenous injection, intravenous drip, subcutaneous, intraperitoneal or intramuscular injection, orally or rectally. Human pharmacokinetics of certain antisense oligonucleotides have been studied. See Zhang et al. *Clinical Pharmacology & Therapeutics* (1995) 58(1), 44–53 incorporated by reference in its entirety. It is within the scale of a person's skill in the art to determine optimum dosages and treatment schedules for such treatment regimens.

Doses of the oligonucleotides or analogs thereof of the present invention in a pharmaceutical dosage unit will be an efficacious, nontoxic quantity selected from the range of 0.1–100 mg/kg of body weight, preferably 0.1–50 mg/kg and more preferably 0.1 to 25 mg/kg. The selected dose is administered to a human patient in need of inhibition of angiogenin expression from 1–6 or more times daily or every other day. Dosage is dependent on severity and responsiveness of the effects of abnormal angiogenesis to be treated, with course of treatment lasting from several days to months or until a cure is effected or a reduction of the effects is achieved. Oral dosage units for human administration generally use lower doses. The actual dosage administered may take into account the size and weight of the patient, whether the nature of the treatment is prophylactic or therapeutic in nature, the age, weight, health and sex of the patient, the route of administration, and other factors.

Pharmaceutical compositions may contain suitable excipients and auxiliaries which facilitate processing of the oligonucleotides into preparations which can be used pharmaceutically. Preferably, the preparations, particularly those which can be administered orally and which can be used for the preferred type of administration, such as tablets, dragees, and capsules, and preparations which can be administered rectally, such as suppositories, as well as suitable solutions for administration parenterally or orally, and compositions which can be administered bucally or sublingually, including inclusion compounds, contain from about 0.1 to about 99 percent by weight of active ingredients, together with the excipient.

The pharmaceutical preparations of the present invention are manufactured in a manner which is itself well known in the art. For example, the pharmaceutical preparations may be made by means of conventional mixing, granulating, dragee-making, dissolving, or lyophilizing processes. The process to be used will depend ultimately on the physical properties of the active ingredient used.

Suitable excipients are, in particular, fillers such as sugars, for example, lactose or sucrose, mannitol or sorbitol, cellulose preparations and/or calcium phosphates, for example, tricalcium phosphate or calcium hydrogen phosphate as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl-starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate, and/or polyethylene glycol. Dragee cores may be provided with suitable coatings which, if desired, may be resistant to gastric juices. For this purpose, concentrated sugar solutions may be used, which may optionally contain gum arabic, talc, polyvinylpyrrolidone, polyethylene, glycol, and/or titanium dioxide, lacquer solutions, and suitable organic solvents or solvent mixtures. In order to produce coatings resistant to gastric juices, solutions of suitable cellulose preparations such as acetylcellulose phthalate or hydroxypropylmethycellulose phthalate, are used. Dyestuffs and pigments may be added to the tablets of dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with filters such as lactose, binders such as starches, and/or lubricants such as talc or magnesium stearate and optionally, stabilizers. In soft capsules, the active compounds are preferably dissolved or suspended in suitable liquids, such as fatty oils, liquid paraffin, or liquid polyethylene glycols. In additions, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols or higher alkanols. In addition, it is also possible to use gelatin rectal capsules which consist of a combination of the active compounds with a base. Possible base materials include, for example liquid triglycerides, polyethylene glycols, or paraffin hydrocarbons.

Suitable formulations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, ethyl oleate or triglycerides. Aqueous injection suspensions may contain substances which increase the viscosity of the suspension including, for example, sodium carboxymethyl cellulose, sorbitol, and/or dextran. Optionally, the suspension may also contain stabilizers.

Additionally, oligonucleotides of the present invention may also be administered encapsulated in liposomes or immunoliposomes, which are pharmaceutical compositions wherein the active ingredient is contained either dispersed or variously present in corpuscles consisting of aqueous concentric layers adherent to lipidic layers. Liposomes are especially active in targeting the oligonucleotides to liver cells. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as dicetylphosphate, stearylamine, or phosphatidic acid, and/or other materials of a hydrophobic nature. The diameters of the liposomes generally range from about 15 nm to about 5 microns.

Antisense in Combination with-Other-Therapies

Published pharmacologic data indicate that phosphorothioate derivatives of oligonucleotides, when administered systemically, are taken up preferentially by the liver (and additionally by the kidney and bone marrow). Angiogenin is known to be a normal component of human plasma and serum synthesized predominantly by the adult liver. Therefore, oligonucleotides effective to inhibit the expression of angiogenin should accumulate in the liver and inhibit the endogenous synthesis of angiogenin and consequently lower its concentration in plasma and serum. The lower plasma/serum levels of angiogenin should then allow for more effective antitumor therapy using any of the angiogenin binding agents described herein that inhibit angiogenin's function by directly binding to the protein, since they will not have to first overcome binding to endogenous, circulating angiogenin before reaching the tumor itself. The use of oligonucleotides to inhibit the expression of angiogenin in combination with other angiogenin binding agents also lowers the potential for toxicity that might result from substantial amounts of circulating angiogenin inhibitor complexes due to the reduced amount of circulating angiogenin.

The oligonucleotides of the present invention are also envisioned to be useful in combination with other tumor targeted therapeutic maneuvers such as chemotherapy, immunotherapy, radiation therapy and the like so as to increase the overall anticancer therapeutic efficacy.

Oligonucleotides as Diagnostic Agents

The oligonucleotides of the present invention are also useful for detection and diagnosis of angiogenin in clinical samples. For example, radio labeled oligonucleotides can be prepared by $^{32}P$ labeling at the 5' end with polynucleotide kinase. Sambrook et al. *Molecular Cloning. A Laboratory Manual*, Cold Spring Harbor Laboratory Press, 1989, Volume 2, pg. 10.59. Radio labeled oligonucleotides are then contacted with tissue or cell samples suspected of containing target nucleic acids and the sample is washed to remove unbound oligonucleotide. Radioactivity remaining in the sample indicates bound oligonucleotide (which in turn indicates the presence of target nucleic acids) and can be quantitated using a scintillation counter or other routine means. Abnormally high levels of target nucleic acids can be detected in this way. Radio labeled oligonucleotides can also be used to perform autoradiography of tissues to determine the localization, distribution and quantitation of target nucleic acids for research, diagnostic or therapeutic purposes. In such studies, tissue sections are treated with radio labeled oligonucleotide and washed as described above, then exposed to photographic emulsion according to routine autoradiology procedures. The emulsion, when developed, yields an image of silver grains over the regions expressing angiogenin.

Analogous assays for fluorescent detection of angiogenin expression can be developed using oligonucleotides of the invention which are conjugated with fluorescein or other fluorescent tag instead of radio labeling. Such conjugations are routinely accomplished during solid phase synthesis using fluorescently labeled amidites or CPG (c.g. fluorescein labeled amidites and CPG available from Glen Research, Sterling Va. Sec. 1993 Catalog of Products for DNA Research, Glen Research, Sterling Va, p. 21).

Each of these assay formats is known in the art. One of skill could easily adapt these known assays for detection of target nucleic acids in accordance with the teachings of the invention providing a novel and useful means to detect levels of nucleic acids encoding angiogenin.

The following examples are set forth as representative of the present invention. These examples are not to be construed as limiting the scope of the invention as these and other equivalent embodiments will be apparent in view of the present disclosure, figures, tables, and accompanying claims.

EXAMPLE 1

Materials

Materials used in the following experimental examples were obtained as follows. Human PC-3 prostate and HT-29 colon tumor cells were obtained from the American Type Culture Collection. MDA-MB-435 human breast tumor and PC-3M human prostate tumor cell lines were obtained from Dr. Isaiah J. Fidler (M.D. Anderson Cancer Center). Human MCF-7 breast cancer cells were obtained from Dr. Marc Lippman (Georgetown University Medical Center). Cell culture supplies were obtained as follow: all tissue culture plastics were from Costar; Dulbecco's modified Eagle's medium (DMEM), Ham's F-12 medium, MEM Eagle medium, trypsin-versene, and Hanks' buffered salt solution (HBSS) were obtained from BioWhittaker; fetal bovine serum (FBS) was from Hyclone. Materials for the enzyme-linked immunosorbent assay (ELISA) were as follows: human angiogenin was isolated from an *Escherichia coli* expression system [Shapiro, R., Harper, J. W., Fox, E. A., Jansen, H-W., Hein, F., and Uhlmann, E. (1988) *Anal. Biochem*. 175,450–461] and was provided by Dr. Robert Shapiro (Harvard Medical School); the anti-human angiogenin mAb 26-2F was obtained by us as described (Mahadevan and Hart, 1990, supra); the rabbit polyclonal anti-human angiogenin antibody R113 was produced by immunization into a rabbit of human angiogenin together with Freund's adjuvant using classical techniques; ELISA plates were from Costar; bovine serum albumin (BSA) and p-nitrophenyl phosphate were from Sigma; alkaline phosphatase-labeled goat anti-rabbit IgG was obtained from Kirkegaard and Perry. Lipofectin was from GibcoBRL. Slow release pellets containing 17 β-estradiol were obtained from Innovative Research of America. Custom-synthesized angiogenin sense and antisense [S]ODNs were from Promega or Boston BioSystems. Outbred, male and female athymic (nu/nu) mice were obtained from Charles River Laboratories and maintained under specific pathogen-free conditions in an environment strictly controlled for temperature and humidity. Matrigel basement membrane matrix was from Collaborative Biomedical Products.

EXAMPLE II

Cell Culture Growth Coditions

Cell cultures used in the following experimental examples are described as follows. All cells were maintained at 37° C. in a humidified, 95% air/5% $CO_2$ environment. HT-29 cells were grown in DMEM containing 5% FBS; PC-3M cells were grown in MEM Eagle medium containing 10% FBS and vitamins; PC-3 cells were cultured in Ham's F-12 containing 7% FBS. All growth medium was supplemented with 2 mM L-glutamine and antibiotics (gentamicin and fungizone). For experiments, cells were harvested with trypsin-versene and counted with either a Coulter counter or by hemacytometry following staining with Trypan blue for viability determination. Prior to injection into mice, cells were first washed twice with HBSS.

EXAMPLE III

Measurement of Angiogenin Leyels

Angiogenin levels in medium conditioned by human tumor cells were measured by a double antibody ELISA as described [Newton, D. L., Xue, Y., Olson, K. A., Fett, J. W., and Rybak, S. M. (1996) *Biochemistry* 35, 545–553]. Anti-human angiogenin mAb 26-2F was coated onto wells of an ELISA plate and blocked with BSA. Dilutions of medium to be tested were then added to the plate and incubated overnight. After washing, rabbit anti-human angiogenin antibody (R113) was added. Bound R113 was detected by adding alkaline phosphatase-labeled goat anti-rabbit IgG followed by the addition of p-nitrophenyl phosphate. The plates were read at 405 nm with a computer-controlled Bio-Tek EL 311 ELISA reader using the associated data analysis program. Angiogenin levels in conditioned medium were quantitated by comparison with a standard curve of human angiogenin.

EXAMPLE IV

Antisense Oligodeoxynucleotides

Angiogenin sense and antisense phosphorothioate oligodeoxynucleotides, [S]ODNs, used in the following experiments were as follows. Two antisense 18-mer [S]ODNs were custom-synthesized by Promega based on the nucleic acid sequences of the angiogenin gene encompassing the AUG initiation codon and transcriptional start site regions and labeled JF2S (SEQ ID NO.: 4) and JF4S (SEQ ID NO.: 5), respectively. In addition, an 18-mer control sense [S]ODN complementary to JF2S (SEQ ID NO.: 4) was synthesized and labeled JF1S (SEQ ID NO.: 3). Their compositions are:

JF1S (SEQ ID NO.: 3) 5'-GAAGAGATGGTGATGGGC-3'

JF2S (SEQ ID NO.: 4) 5'-GCCCATCACCATCTCTTC-3'

JF4S (SEQ ID NO.: 5) 5'-ACACGGCATCATGAATCA-3'

Other preferred oligonucleotides include the following:

JF6S (SEQ ID NO.: 6) 5'-CCAGGGGCCCGCTGGTTA-3'

JF8S (SEQ ID NO.: 7) 5'-ACCAAATTTTATATTCTA-3'

JF10S (SEQ ID NO.: 8) 5'-CAGGCCCATCACCATCAC-3'

JF12S (SEQ ID NO.: 9) 5'-GCCCAGGCCCATCACCAT-3'

JF13S (SEQ ID NO.: 10) 5'-TCTCTGACACGGCATCAT-3'

JF6S (SEQ ID NO.: 6) encompasses the 3'-termination site, JF8S (SEQ ID NO.: 7) encompasses the 5'-"TATA" box site, JF10S (SEQ ID NO.: 8) and JF12S (SEQ ID NO.: 9) encompass the "AUG" translational start site and comprise variations of sequence from JF2S (SEQ ID NO.: 4), and JF13S (SEQ ID NO.: 10) encompasses the 5'-transcriptional start site and comprises a variation of sequence from JF4S (SEQ ID NO.: 5).

It is to be understood that additional oligonucleotides within the scope of the present invention can be prepared by first selecting a target sequence anywhere along the known nucleic acid sequence of the angiogenin gene. An oligonucleotide complementary to the target sequence can then be prepared based upon the known complementary relationship between nucleic acids. In this manner, any number of oligonucleotides complementary to target sequences of the angiogenin gene can be prepared and their ability to inhibit the expression of the angiogenin gene can than be determined based upon the teachings presented herein.

EXAMPLE V

Antisense Oligodeoxynucleotides Inhibit Expression of Angiogenin

Experiments initially performed in vitro were aimed at assessing whether these angiogenin antisense reagents were effective inhibitors of angiogenin synthesis by prostatic carcinoma cell lines. Efficient transfection of ODNs in vitro requires the presence of a cationic lipid, one of which, lipofectin, was obtained from GibcoBRL. Details of the lipofectin transfection procedure are provided by the manufacturer, GibcoBRL. In a first experiment, the results of which are shown in FIG. 2, panel A, PC-3 prostatic carcinoma cells ($5 \times 10^5$ cells in 35 mm dishes) were treated in vitro for 20 hr with lipofectin (5 $\mu$l) alone (control, white bar) or lipofectin plus JF2S (SEQ ID NO.: 4) (0.5 $\mu$M) (black bar). The growth medium was then replaced and the cells allowed to recover for 24 hr. After that period the cells were harvested and counted and the conditioned medium was assayed for angiogenin levels by ELISA. The amount of angiogenin per cell number for the antisense-treated cultures in percent compared with control-treated cells (100%) is plotted. The results of a second in vitro experiment under the same conditions is plotted in panel B of FIG. 2. The data indicate that angiogenin production in vitro as a function of cell number decreased by 18–33% by treating with the combination of lipofectin plus JF2S (SEQ ID NO.: 4) in comparison with the treatment with lipofectin alone.

Figure 3A:
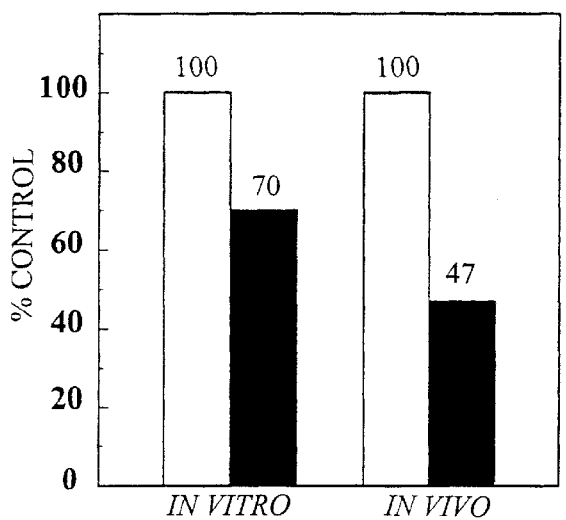
FIGS. 3A and 3B are graphs depicting the inhibition by angiogenin antisense [S]ODN JF2S (SEQ ID NO.: 4) of angiogenin expression by HT-29 tumor cells in vitro and their subsequent growth in vivo.
Figure 3B:
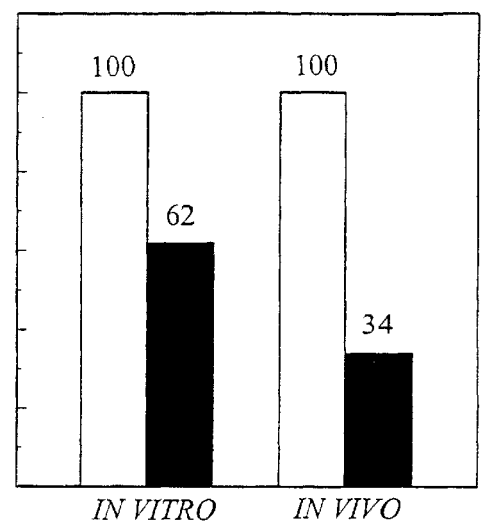
Figure 4:
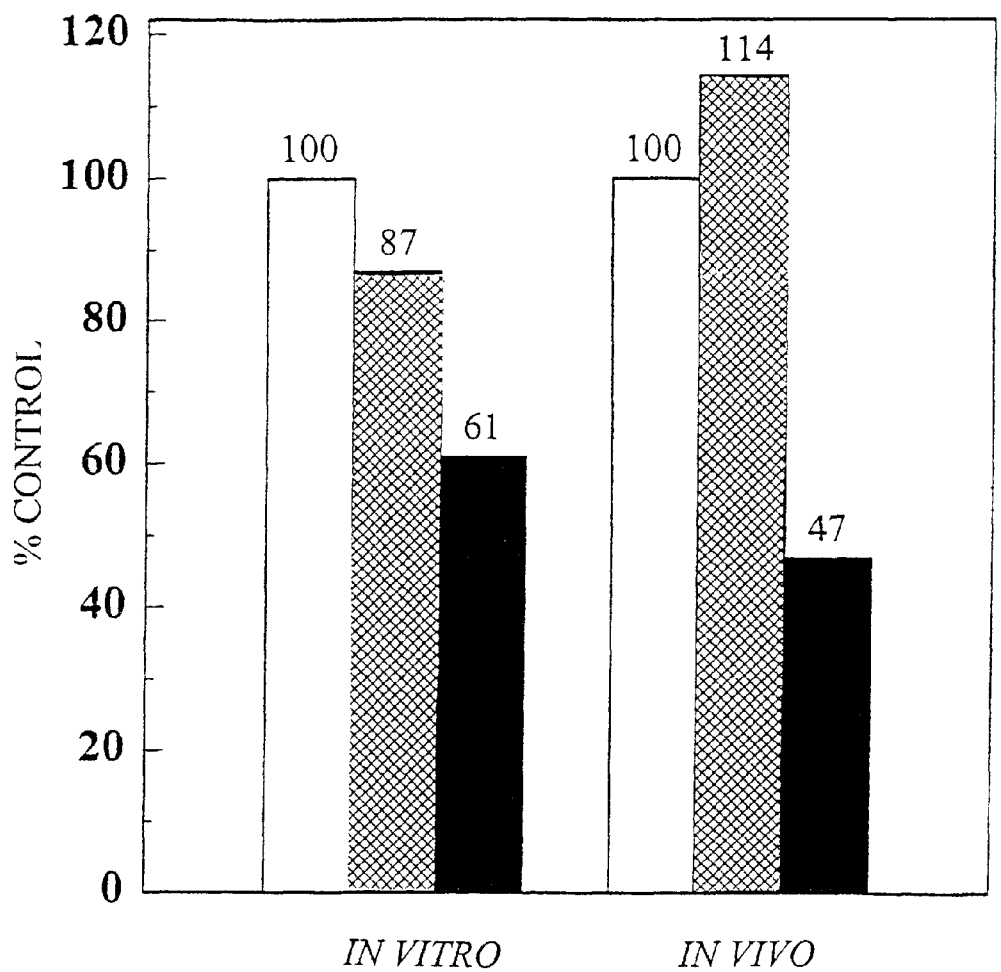
FIG. 4 is a graph showing treatment of HT-29 tumor cells in vitro with antisense [S]ODN JF2S (SEQ ID NO.: 4) and control sense [S]ODN JF1S (SEQ ID NO.: 3) and their subsequent growth in vivo.
Figure 5:
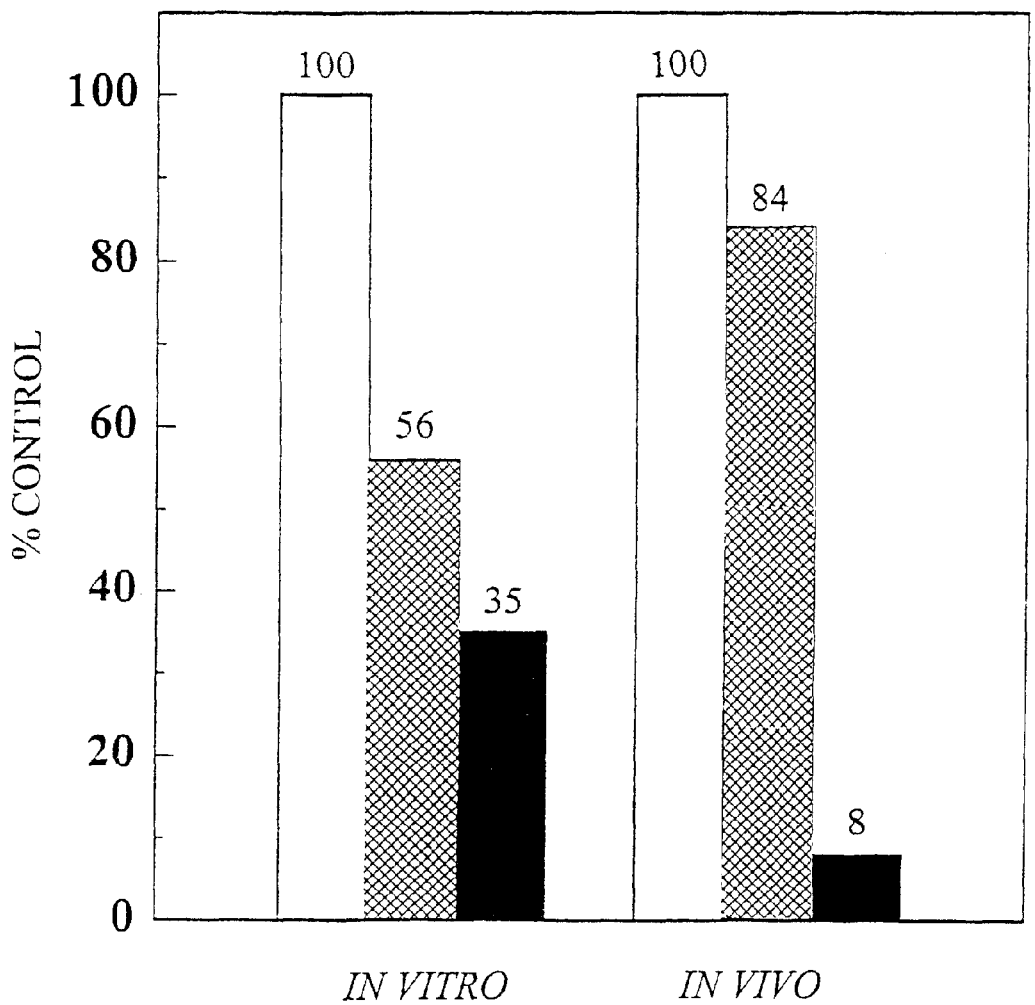
FIG. 5 is a graph showing treatment of PC-3 tumor cells in vitro with antisense [S]ODN JF2S (SEQ ID NO.: 4) and control sense [S]ODN JF1S (SEQ ID NO.: 3) and their subsequent growth in vivo.
Figure 6:
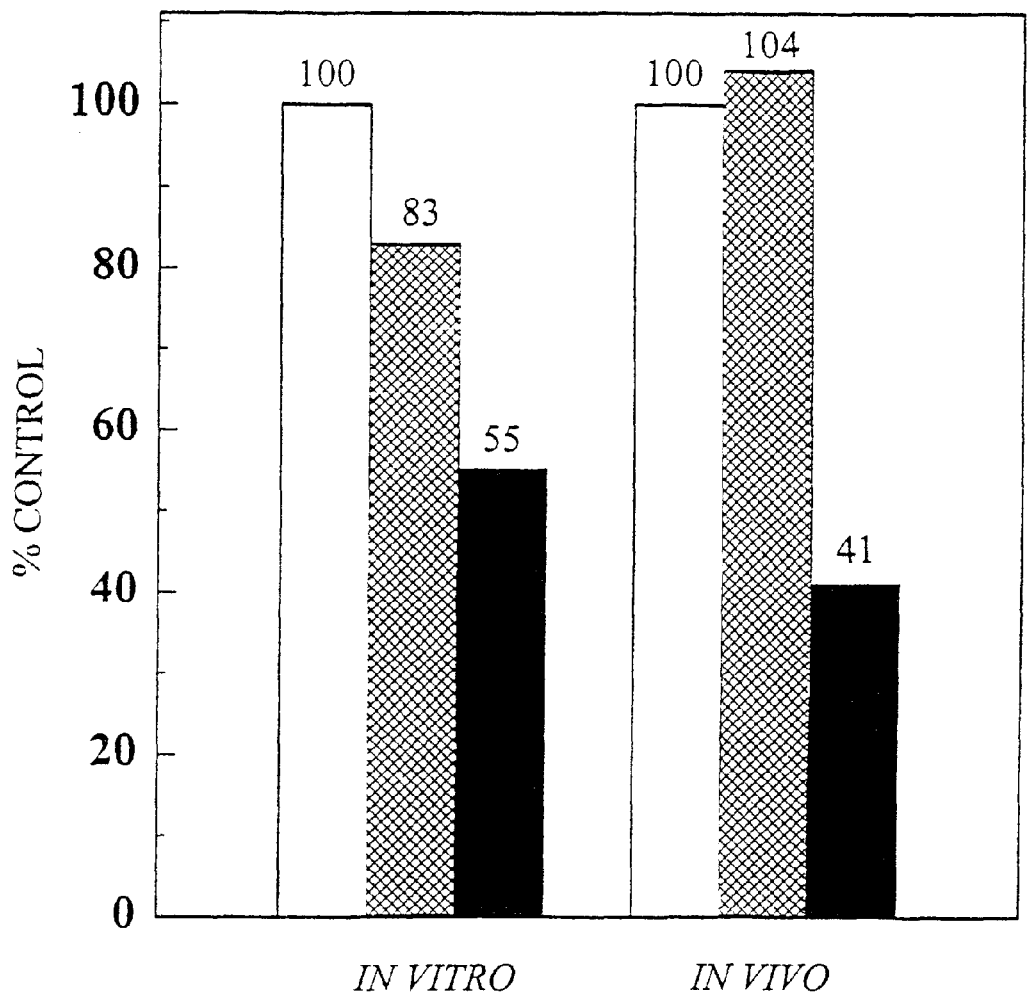
FIG. 6 is a graph showing treatment of MDA-MB-435 tumor cells in vitro with antisense [S]ODN JF2S (SEQ ID NO.: 4) and control sense [S] ODN JF1S (SEQ ID NO.: 3) and their subsequent growth in vivo.
Figure 7:
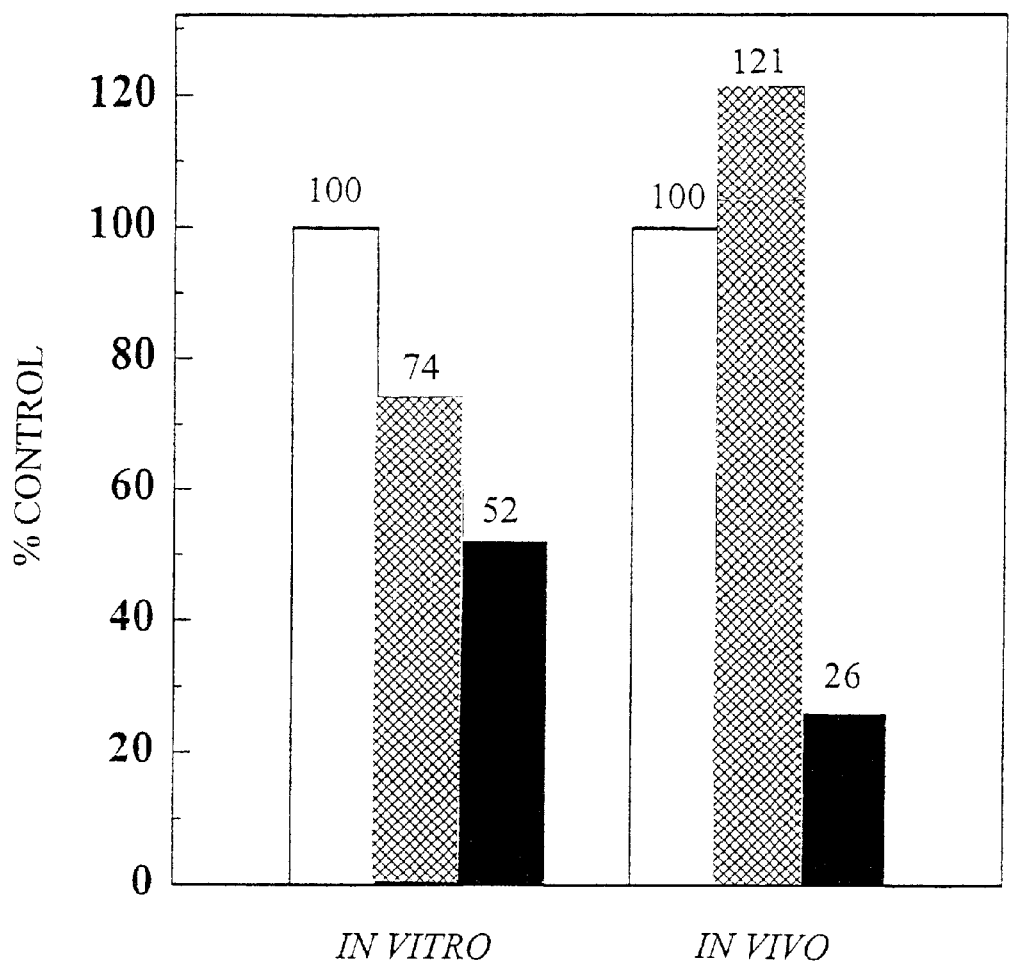
FIG. 7 is a graph showing treatment of PC-3M tumor cells in vitro with antisense [S]ODN JF2S (SEQ ID NO.: 4) and control sense [S]ODN JF1S (SEQ ID NO.: 3) and their subsequent growth in vivo.

FIG. 3 shows the results of a similar experiment using HT-29 colon adenocarcinoma cell line. In the first experiment, the results of which are plotted in FIG. 3 panel A, HT-29 cells ($5 \times 10^5$ cells in 35 mm dishes) were treated in vitro for 20 hr with lipofectin (5 $\mu$l) alone (control, white bar) or lipofectin plus JF2S (SEQ ID NO.: 4) (0.5 $\mu$M) (black bar). The growth medium was then replaced and the cells allowed to recover for 24 hr. After that period the cells were harvested and counted and the conditioned medium was assayed for angiogenin levels by ELISA. The amount of angiogenin per cell number for the antisense-treated cultures in percent compared with control-treated cells (100%) is plotted. The results of a second in vitro experiment under the same conditions is plotted in panel B of FIG. 3. The data indicates that angiogenin production in vitro as a function of cell number decreased by 30–38% by treating with the combination of lipofectin plus JF2S (SEQ ID NO.: 4) in comparison with the treatment with lipofectin alone.

The data demonstrates that for both PC-3 and HT-29 tumor cell types angiogenin production in vitro as a function of cell number was decreased by treating with the combination of lipofectin plus JF2S (SEQ ID NO.: 4) in comparison to treatment with lipofectin alone.

EXAMPLE VI

Antisense Oligodeoxynucleotides Reduce Tumor Size

The ex vivo-treated PC-3 tumor cells of Example V were injected s.c. into athymic mice ($2.5 \times 10^5$ cells/mouse; 5 mice/group) with the usual co-administration of a 1:2 proportion of Matrigel for reproducible cell growth of this cell line. After 8 days, by which time the control tumors had attained a size in excess of that supportable by diffusion and were therefore dependent upon angiogenesis, the mice were sacrificed and the tumors were excised and weighed. The average weight of the tumors resulting from injection of the antisense-treated cells in percent was compared with that of the control group's tumors (100%) and shown in FIG. 2 (panels A & B, in vivo). Tumors arising from injection of JF2S (SEQ ID NO.: 4)-treated PC-3 cells were both 31–54% smaller in average weight than the tumors which developed from their respective control-treated cells. Of additional importance, in the experiment represented by FIG. 2 panel B, 1 mouse out of 5 did not develop an observable tumor by the time of sacrifice.

The ex vivo-treated HT-29 tumor cells were also injected s.c. into athymic mice ($2.5 \times 10^5$ cells/mouse; 5 mice/group). After 15 days, by which time the control tumors had attained a size in excess of that supportable by diffusion and were therefore dependent upon angiogenesis, the mice were sacrificed and the tumors were excised and weighed. The average weight of the tumors resulting from injection of the antisense-treated cells in percent was compared with that of the control group's tumors (100%) and shown in FIG. 3 (panels A & B, in vivo). Tumors arising from injection of JF2S (SEQ ID NO.: 4)-treated PC-3 cells were both 53–66% smaller in average weight than the tumors which developed from their respective control-treated cells. Of additional importance, in the experiment represented by FIG. 3 panel A, 1 mouse out of 5 did not develop an observable tumor by the time of sacrifice.

These results indicate that a correlation exists between decreased tumor growth in vivo and decreased angiogenin production by tumor cells treated in vitro with JF2S (SEQ ID NO.: 4).

FIGS. 4, 5, 6 and 7 show the results of in vitro experiments in which HT-29, PC-3, MDA-MB-435 or PC-3M tumor cells, respectively, were treated with lipofectin alone or lipofectin with either antisense [S]ODN JF2S (SEQ ID NO.: 4) or control sense [S]ODN JF1S (SEQ ID NO.: 3). The amount of angiogenin per cell number for the antisense-treated (black bar) and sense-treated (grey bar) cultures in percent compared with control lipofectin-treated cells (100%) (white bar) is plotted. Angiogenin production in vitro as a function of cell number decreased by 39% (HT-29), 65% (PC-3), 45% (MDA-MB-435) and 48% (PC-3M) by treating with the combination of lipofectin plus antisense [S]ODN JF2S (SEQ ID NO.: 4) in comparison with treatment with lipofectin alone. Treatment with control sense [S]ODN JF1S (SEQ ID NO.: 3) plus lipofectin resulted in a decrease of 13% (HT-29), 44% (PC-3), 17% (MDA-MB-435) and 26% (PC-3M) in comparison with treatment with lipofectin alone. These same ex vivo-treated tumor cells were subsequently injected into athymic mice [HT-29 cells: $2.5 \times 10^5$ cells/mouse (5 mice/group); PC-3 cells: $1.25 \times 10^5$ cells/mouse injected s.c., mixed with a 1:2 proportion of Matrigel (5 mice/group); MDA-MB-435 cells: $7.5 \times 10^5$ cells/mouse, injected s.c. into the mammary fat pad (5 mice/group, except for the group receiving the antisense [S]ODN JF2S (SEQ ID NO.: 4)-treated cells, in which there were 7 mice); PC-3M: $2.5 \times 10^5$ cells/mouse injected s.c., mixed with a 1:2 proportion of Matrigel (5 mice/group)]. After 17 (HT-29), 25 (PC-3), 30 (MDA-MB-435) or 17 (PC-3M) days, by which time the control tumors had attained a size in excess of that supportable by diffusion and were therefore dependent upon angiogenesis, the mice were sacrificed and the tumors were excised and weighed. The average weight of the tumors resulting from injection of antisense [S]ODN JF2S (SEQ ID NO.: 4)-treated cells in percent was compared with that of the control group's tumors (100%) and shown in FIG. 4 (HT-29), FIG. 5 (PC-3), FIG. 6 (MDA-MB-435) and FIG. 7 (PC-3M) (in vivo). Tumors arising from injection of antisense [S]ODN JF2S (SEQ ID NO.: 4)-treated tumor cells were 53% (HT-29), 92% (PC-3), 59% (MDA-MB-435) and 74% (PC-3M) smaller in average weight than the tumors which developed from the cells treated with lipofectin alone. Tumors arising from PC-3 cells treated with the control sense [S]ODN JF1S (SEQ ID NO.: 3) were 16% (FIG. 5, in vivo) smaller than those tumors which developed from cells treated with lipofectin alone. Tumors arising from HT-29, MDA-MB-435 or PC-3M cells treated with the control sense [S]ODN JF1S (SEQ ID NO.: 3) were actually 14%, 4% or 21% larger, respectively, than those tumors which developed from the cells treated with lipofectin alone. In all three experiments all mice receiving either control lipofectin or sense [S]ODN JF1S (SEQ ID NO.: 3)-treated cells developed tumors. Among those mice receiving cells treated with antisense [S]ODN JF2S (SEQ ID NO.: 4), tumors did not develop by the time of termination of the experiments in 1 out of 5 (HT-29 cells), 4 out of 5 (PC-3 cells), 1 out of 7 (MDA-MB-435 cells) and 2 out of 5 (PC-3M cells) mice. These results further indicate that a correlation exists between decreased tumor growth in vivo and decreased angiogenin production by tumor cells treated in vitro with antisense [S]ODN JF2S (SEQ ID NO.: 4).

Figure 8:
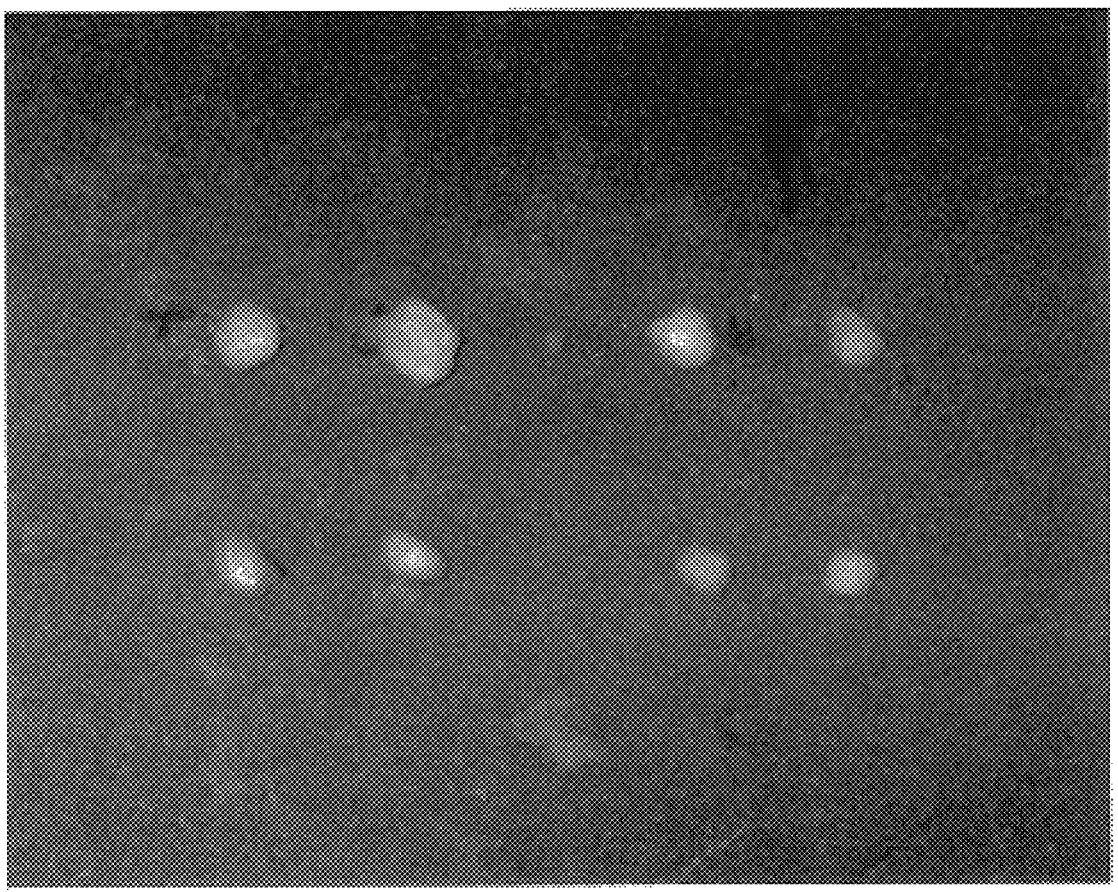
FIG. 8 is a photograph showing the differences in the presence and size of angiogenin antisense [S]ODN (JF2S (SEQ ID NO.: 4)) and control (lipofectin)-treated PC-3 tumors excised from athymic mice.

FIG. 8 is a photograph of the actual tumors excised from mice injected with PC-3 cells treated in vitro with either the antisense [S]ODN, JF2S (SEQ ID NO.: 4), (bottom row) or control lipofectin (top row) as described in Example V and as shown in FIG. 2 panel B. This shows the differences between these two groups of tumors in both size and occurrence. One mouse in the antisense-treated group (bottom row) did not develop a tumor while those that did develop were on average much smaller size than tumors arising from control-treated cells (top row).

Figure 9:
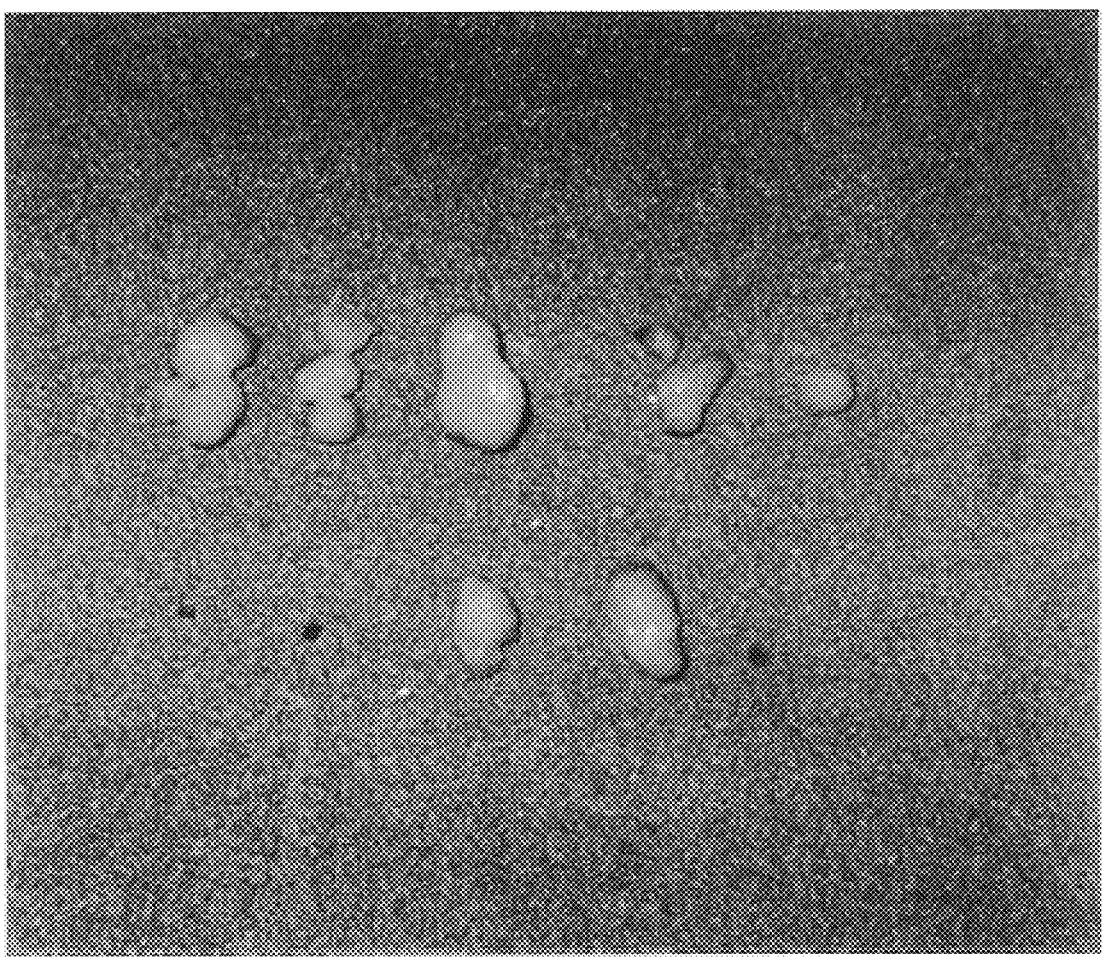
FIG. 9 is a photograph showing the differences in the presence and size of angiogenin antisense [S]ODN (JF2S (SEQ ID NO.: 4)) and control (lipofectin)-treated HT-29 tumors excised from athymic mice.
Figure 10:
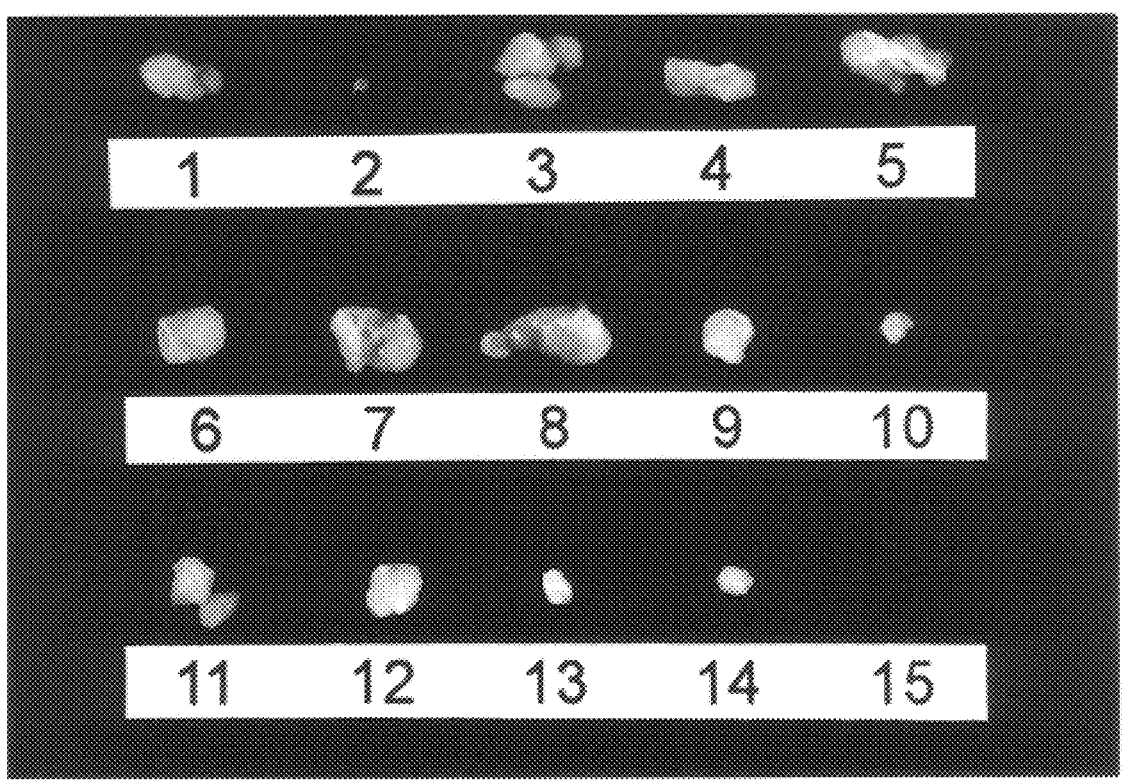
FIG. 10 is a photograph showing the differences in the presence and size of angiogenin antisense [S]ODN (JF2S (SEQ ID NO.: 4)), control sense [S]ODN (JF1S (SEQ ID NO.: 3)) and control (lipofectin)-treated HT-29 tumors excised from athymic mice.
Figure 11:
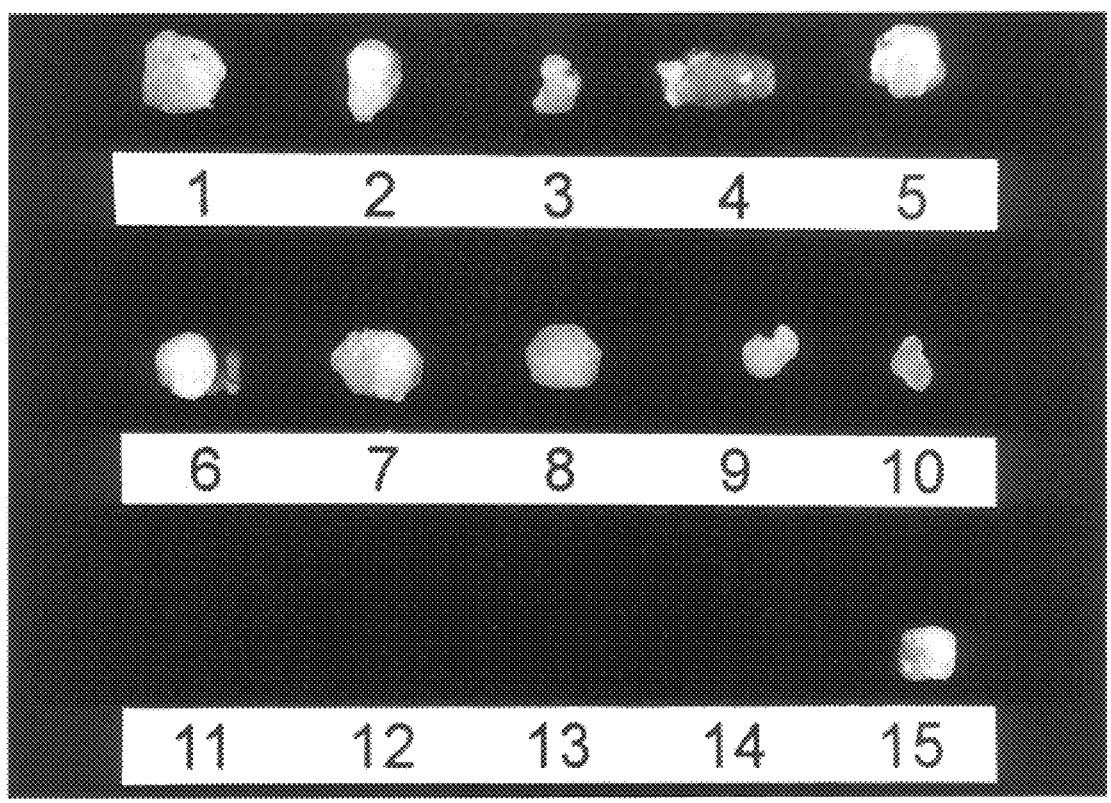
FIG. 11 is a photograph showing the differences in the presence and size of angiogenin antisense [S]ODN (JF2S (SEQ ID NO.: 4)), control sense [S]ODN (JF1S (SEQ ID NO.: 3)) and control (lipofectin)-treated PC-3 tumors excised from athymic mice.
Figure 12:
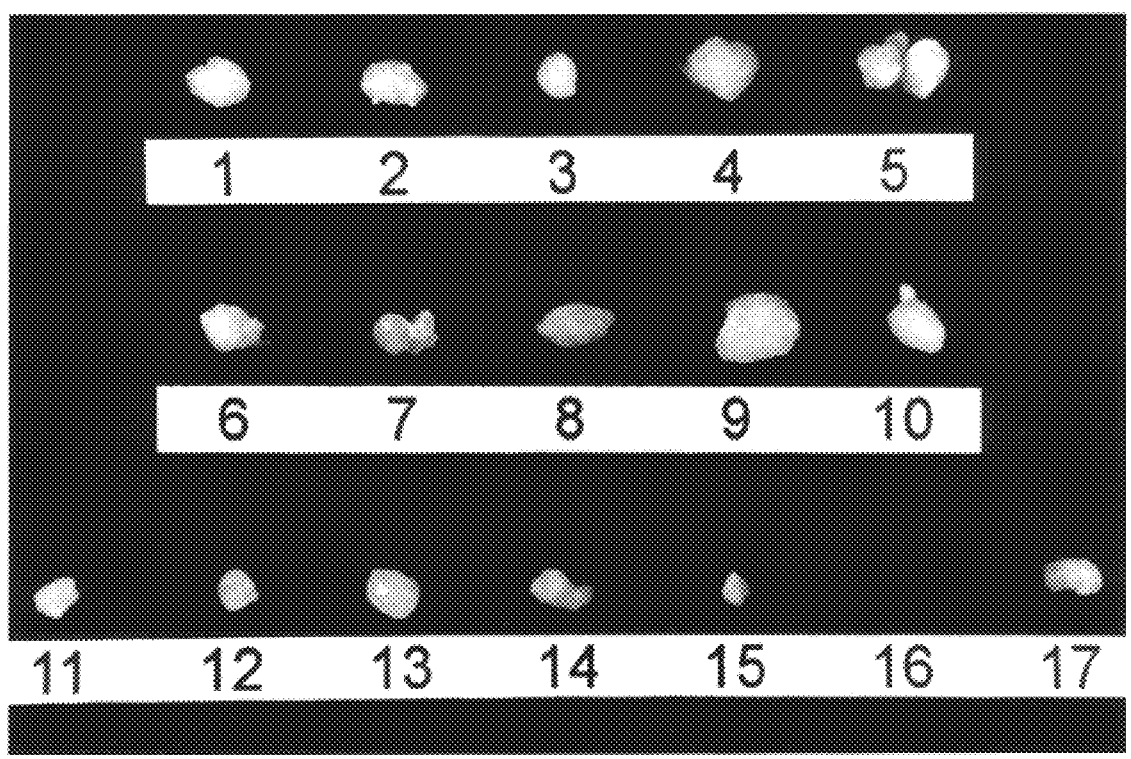
FIG. 12 is photograph showing the differences in the presence and size of angiogenin antisense [S]ODN (JF2S (SEQ ID NO.: 4)), control sense [S]ODN (JF1S (SEQ ID NO.: 3)) and control (lipofectin)-treated MDA-MB-435 tumors excised from athymic mice.
Figure 13:
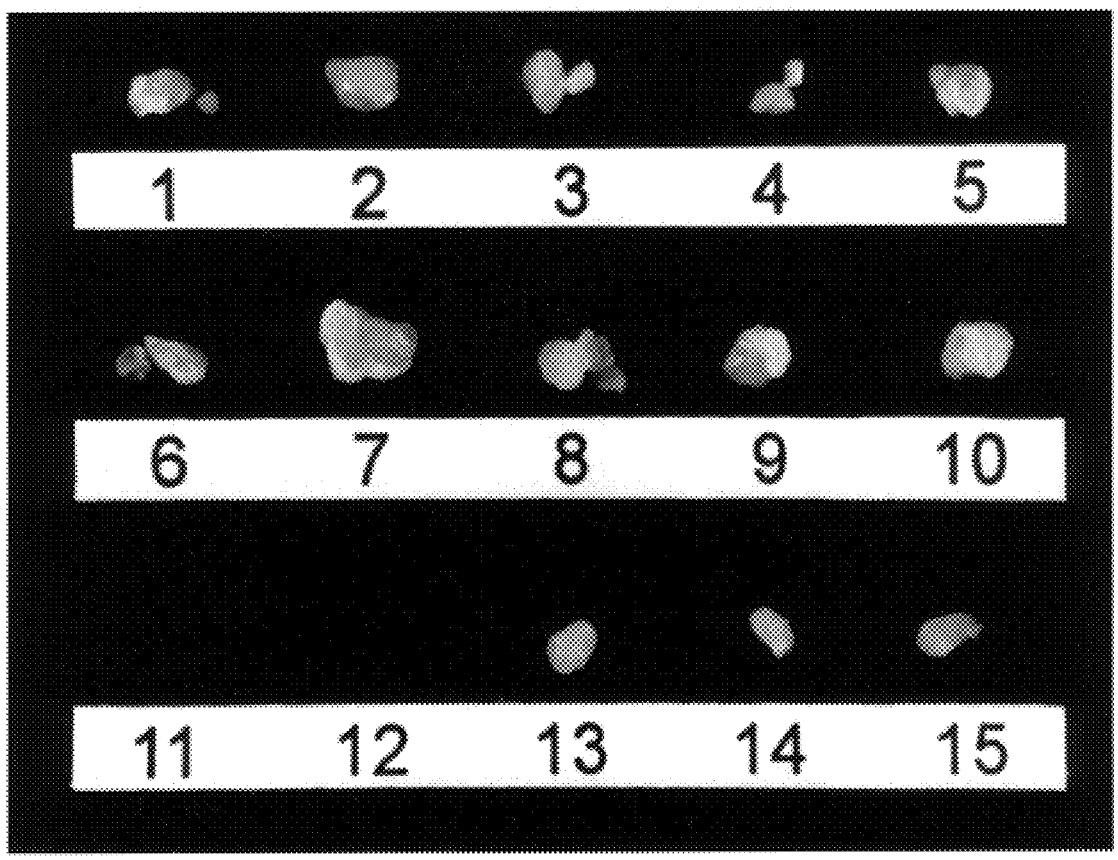
FIG. 13 is a photograph showing the differences in the presence and size of angiogenin antisense [S]ODN (JF2S (SEQ ID NO.: 4)), control sense [S]ODN (JF1 S (SEQ ID NO.: 3)) and control (lipofectin)-treated PC-3M tumors excised from athymic mice.

FIG. 9 is a photograph of the actual tumors excised from mice injected with HT-29 cells treated in vitro with either the antisense [S]ODN, JF2S (SEQ ID NO.: 4) (bottom row) or control lipofectin (top row) as described in Example V and as shown in FIG. 3 panel B. Once again the differences between these two groups of tumors in size is evident, with the tumors developing from the lipofectin plus JF2S (SEQ ID NO.: 4)-treated cells being much smaller on average than those tumors developing from HT-29 tumor cells treated with lipofectin alone. In particular, three of the tumors produced by HT-29 tumor cells treated with JF2S (SEQ ID NO.: 4) were extremely small in size.

Photographs of the actual tumors excised from the mice in experiments shown in FIGS. 4, 5, 6 and 7 are shown in FIGS. 10, 11, 12 and 13, respectively. In each case the photograph shows the tumors resulting from injection of cells treated in vitro with either antisense [S]ODN JF2S (SEQ ID NO.: 4) (bottom row), sense control [S]ODN JF1S (SEQ ID NO.: 3) (middle row) or control lipofectin (top row). The average size of the two groups of control tumors arising from tumor cells treated with either the sense [S]ODN JF1S (SEQ ID NO.: 3) or lipofectin alone is essentially equivalent, while the average size of those tumors arising from the tumor cells treated with the antisense [S]ODN JF2S (SEQ ID NO.: 4) were significantly smaller than either of these two control groups. In fact, tumors did not develop by the termination of the experiments in 1 out of 5 (HT-29 cells, FIG. 10), 4 out of 5 (PC-3 cells, FIG. 11), 1 out of 7 (MDA-MB-435 cells, FIG. 12) and 2 out of 5 (PC-3M cells, FIG. 13) mice receiving cells treated with antisense [S]ODN JF2S (SEQ ID NO.: 4).

From these studies the conclusion can again be drawn that angiogenin is indeed critical for the growth/establishment of tumors in this mouse model, further validating the proposition that anti-angiogenin therapies are effective for treatment of cancer clinically.

EXAMPLE VII

Figure 14:
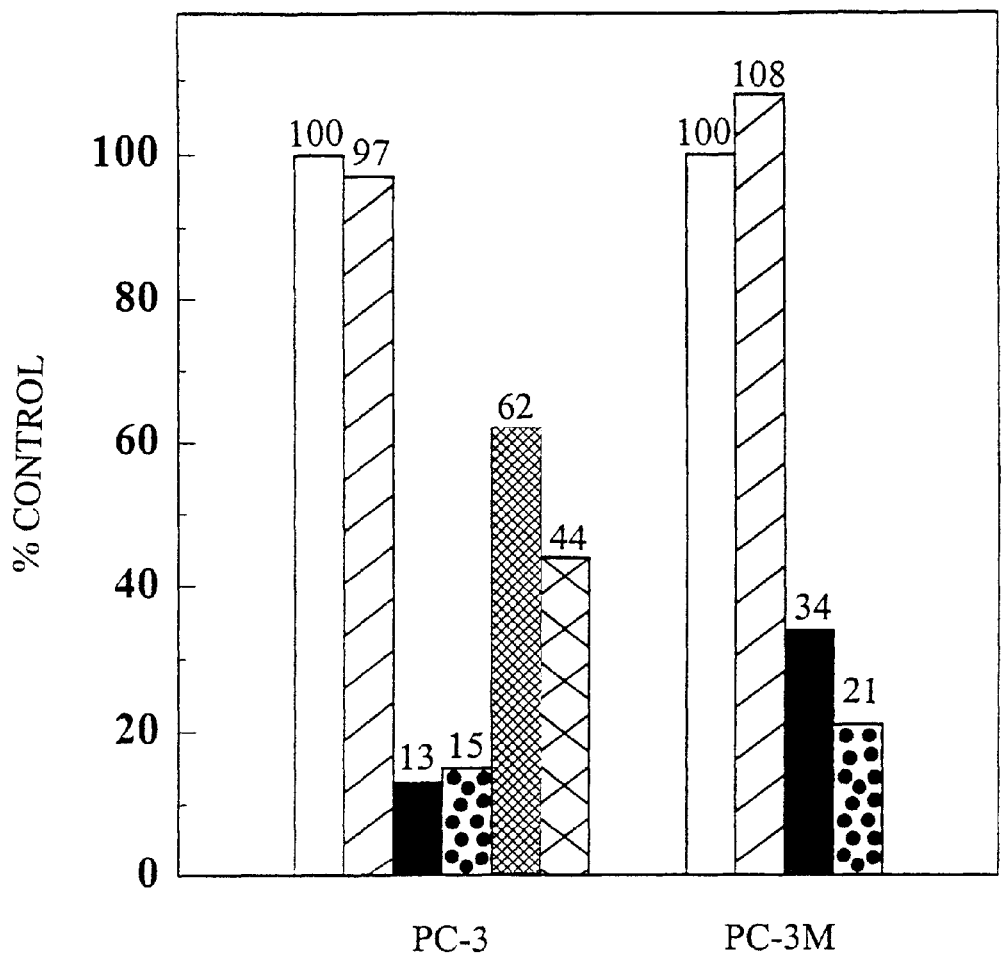
FIG. 14 is a graph showing inhibition of the expression of angiogenin by PC-3 and PC-3M tumor cell lines in culture using the two angiogenin antisense [S]ODNs, JF2S (SEQ ID NO.: 4) and JF4S (SEQ ID NO.: 5).

In two further experiments, shown in FIG. 14 panels A and B, the amount of angiogenin produced by PC-3 cells in vitro could be further decreased by slightly adjusting the conditions of transfection with antisense JF2S (SEQ ID NO.: 4). The figure also shows that JF2S (SEQ ID NO.: 4) can additionally inhibit angiogenin production by PC-3M tumors cells and that another angiogenin antisense [S]ODN, JF4S (SEQ ID NO.: 5), also can inhibit the synthesis of angiogenin by both PC-3 and PC-3M cells in vitro. PC-3 (panel A) or PC-3M (panel B) cells were treated for 20 hr with HBSS as diluent control (white bars), lipofectin (5 μl) alone (control, single cross-hatched bars), lipofectin plus JF2S (SEQ ID NO.: 4) [(0.5—(black bars) or 1.0 μM (dotted bars)], or lipofectin plus JF4S (SEQ ID NO.: 5) [(0.5—(grey bars) or 1.0 μM (double crossed hatched bars)]. The growth medium was then replaced and the cells allowed to recover for 48 hr at which time the cells were harvested and counted and the conditioned medium was assayed for angiogenin levels by ELISA. The amount of angiogenin per cell number for each group in percent compared to that of the HBSS-treated control group (100%) is plotted. This shows that treatment with antisense JF2S (SEQ ID NO.: 4), under these conditions, was now able to inhibit the synthesis of angiogenin by PC-3 cells by about 87% as compared with HBBS-treated cells (panel A). JF2S (SEQ ID NO.: 4) also substantially inhibits angiogenin production by a third tumor cell line PC-3M (panel B). Panels A & B also show that a second angiogenin antisense reagent directed toward the transcriptional start site of the angiogenin gene, JF4S (SEQ ID NO.: 5), also effectively interferes with angiogenin production by both PC-3 and PC-3M tumor cells. Lipofectin alone has essentially no effect on angiogenin levels secreted by either of the two cell types (panels A & B). Importantly, treatment with a control "sense" sequence [S]ODN complementary to JF2S (SEQ ID NO.: 4), i.e. JF1S (SEQ ID NO.: 3), did not result in decreased angiogenin production by PC-3 cells (not shown).

EXAMPLE VIII

Figures 15A, 15B:
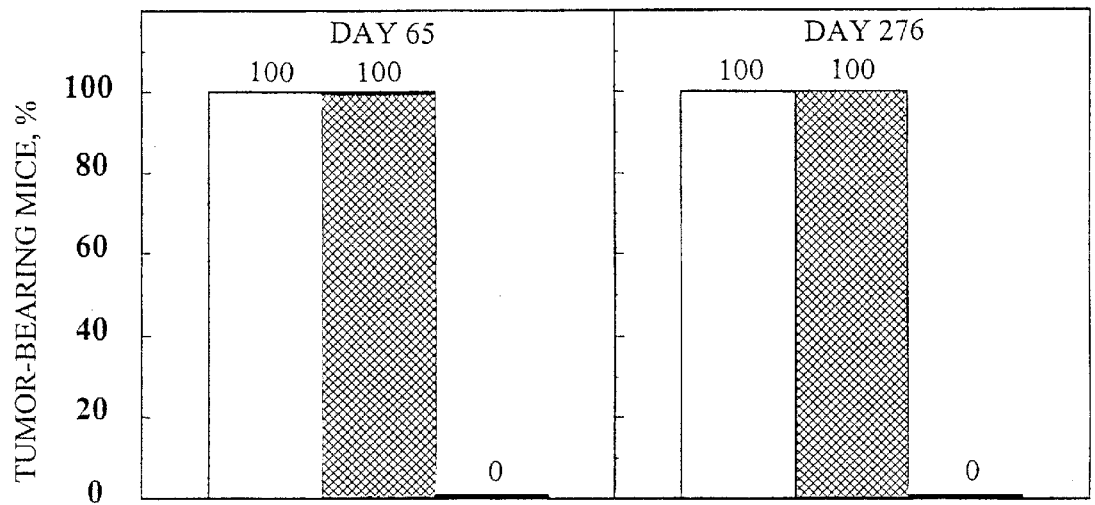
FIGS. 15A, B, and C are graphs showing in vivo therapy of PC-3 tumors with angiogenin antisense [S]ODN JF2S (SEQ ID NO.: 4), control sense [S]ODN JFI S (SEQ ID NO.: 3) and PBS diluent control in three separate experiments.
Figure 15C:
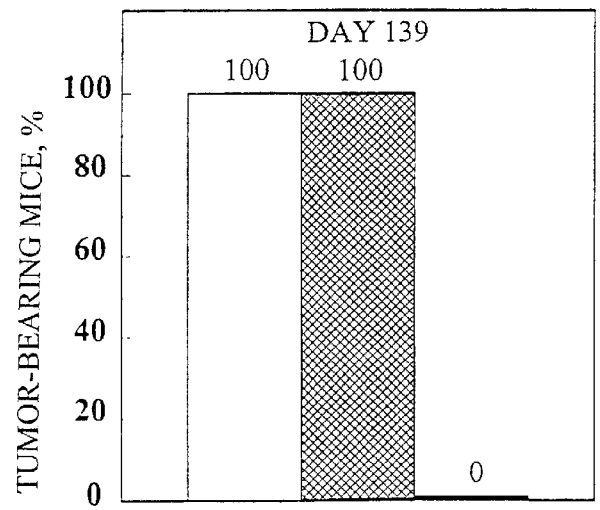

FIG. 15 shows the results obtained in three separate therapy experiments. Each experiment was conducted as follows. On day 0, mixtures of PC-3 tumor cells ($1\times10^4$ cells/mouse) with either antisense [S]ODN JF2S (SEQ ID NO.: 4) (200 μg/mouse), control sense [S]ODN JF1S (SEQ ID NO.: 3) (200 μg/mouse) or PBS (as diluent control) were injected s.c., together with a 1:2 proportion of Matrigel to other components into male athymic mice. Treatment was continued for 48 days as follows: day 1–6, antisense [S]ODN JF2S (SEQ ID NO.: 4) (100 μg/mouse), control sense [S]ODN JF1S (SEQ ID NO.: 3) (100 μg/mouse) or PBS as diluent control injected daily s.c. 6 times per week; days 7–20: antisense [S]ODN JF2S (SEQ ID NO.: 4) (50 μg/mouse), control sense [S]ODN JF1S (SEQ 5 ID NO.: 3) (50 μg/mouse) or PBS as diluent control injected daily s.c. 6 times per week; days 21–49: antisense [S]ODN JF2S (SEQ ID NO.: 4) (50 μg/mouse), control sense [S]ODN JF1S (SEQ ID NO.: 3) (50 μg/mouse) or PBS as diluent control injected daily s.c. 4 times per week. Mice were examined twice a week for the presence of a palpable tumor. After day 49, treatment was stopped.

FIG. 15, panels A, B, and C show the percentage of mice bearing a palpable tumor in each of the antisense [S]ODN JF2S (SEQ ID NO.: 4)-treated (black bar) and control sense [S]ODN JF1S (SEQ ID NO.: 3)-treated (grey bar) groups compared with the PBS diluent control-treated group (white bar, 100%) for three separate, independent experiments. In experiment 1 (panel A), no tumors were observed in any of the antisense [S]ODN JF2S (SEQ ID NO.: 4)-treated mice as of day 65, the day at which the mice were sacrificed. In contrast, all of the mice treated with either control sense [S]ODN JF1S (SEQ ID NO.: 3) or PBS as diluent control exhibited palpable tumors at the time of sacrifice on day 65. In experiment 2, the mice treated with control sense [S]ODN JF1S (SEQ ID NO.: 3) or PBS all exhibited tumors by day 49, and were subsequently sacrificed. However, no tumors were observed at that time in any of the mice treated with the antisense [S]ODN JF2S (SEQ ID NO.: 4). These mice were kept for observation with no further treatment until day 276; no tumors were observed in any of these mice during this period. In experiment 3, the mice treated with control sense [S]ODN JF1S (SEQ ID NO.: 3) or PBS also all exhibited tumors by day 49 and were then sacrificed. The mice treated in this experiment with antisense [S]ODN JF2S (SEQ ID NO.: 4) did not develop tumors during a subsequent observation period, without further treatment, until sacrifice on day 139. In experiments 1 and 2 the [S]ODNs used for treatment were prepared by Promega Corp., while in experiment 3 the [S]ODNs were prepared by Boston BioSystems. Thus in three separate experiments treatment with the antisense [S]ODN JF2S (SEQ ID NO.: 4) was shown to prevent the appearance of PC-3 human tumors after injection of these tumor cells into athymic mice.

Figure 16:
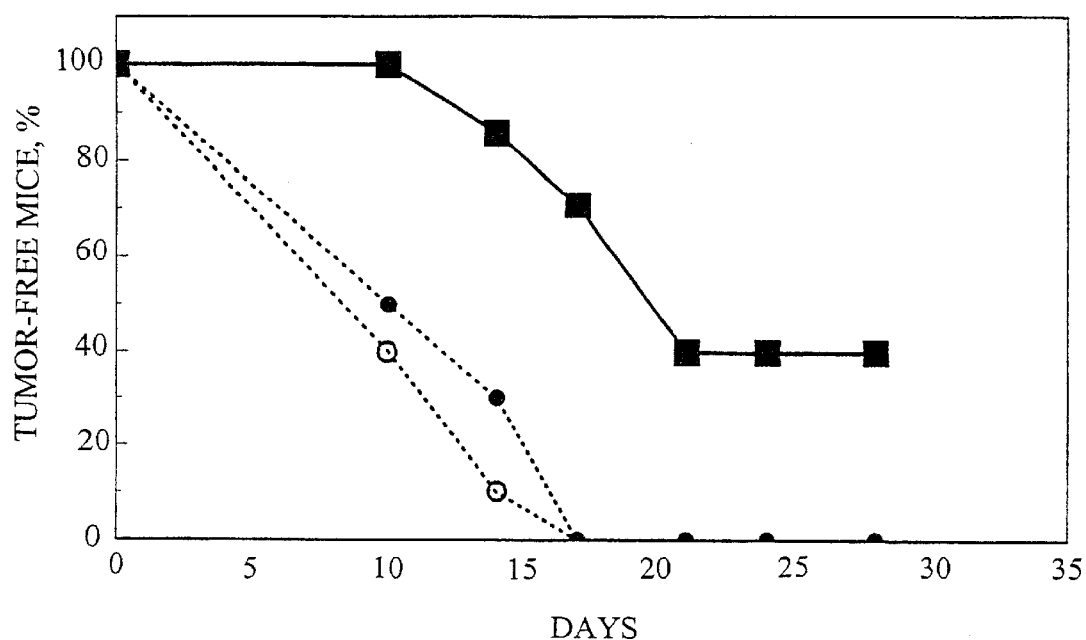
FIG. 16 is a graph showing in vivo therapy of MDA-MB-435 tumors with angiogenin antisense [S]ODN JF2S (SEQ ID NO.: 4), control sense [S]ODN JF1S (SEQ ID NO.: 3) and PBS diluent control.
Figure 17:
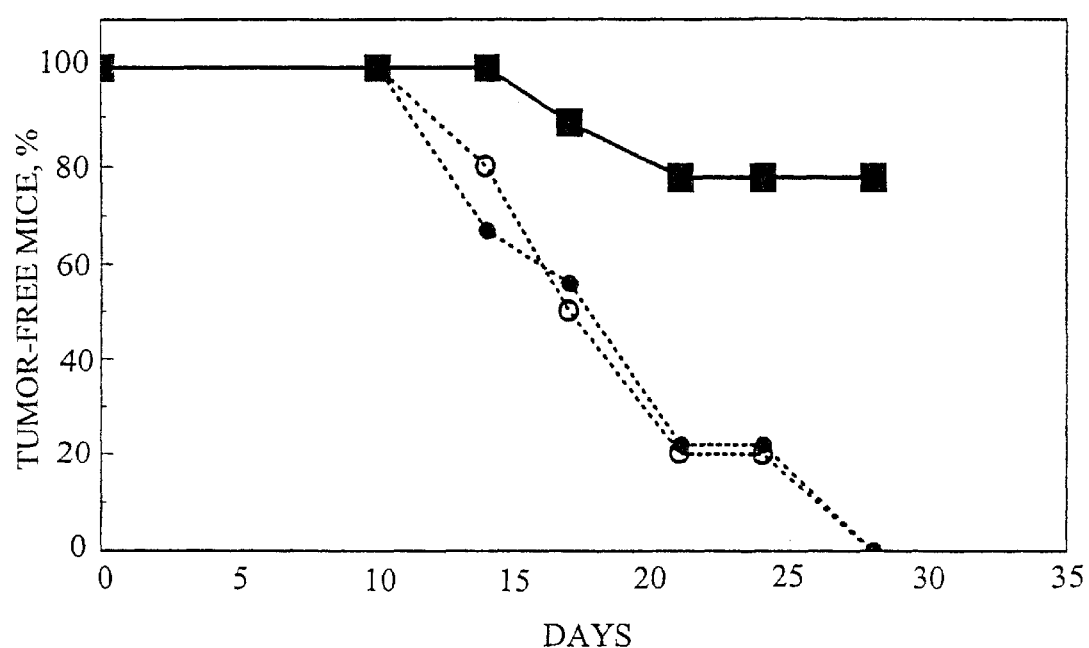
FIG. 17 is a graph showing in vivo therapy of MCF-7 tumors with angiogenin antisense [S]ODN JF2S (SEQ ID NO.: 4), control sense [S]ODN JF1S (SEQ ID NO.: 3) and PBS diluent control.

FIGS. 16 and 17 show the results of similar in vivo therapy experiments using human breast tumor MDA-MB-435 or MCF-7 cells, respectively. The former cell line is estrogen-independent, while the latter is estrogen-dependent. In these experiments the source of the [S]ODNs used for therapy was Boston BioSystems. Tumor cells ($5\times10^5$ MDA-MB-435 cells/mouse or $2\times10^6$ MCF-7 cells/mouse) were injected into the surgically-exposed mammary fat pad behind the left front leg of female athymic mice. In the case of the estrogen-dependent MDF-7 cell line a slow release (60 day) estrogen pellet containing 0.72 mg of 17 β-estradiol was inserted s.c. within 1 cm of the area of tumor cell injection as an exogenous source of estrogen. Within 5 minutes of the tumor cell injection, mice were treated by s.c. injection in the area of the tumor cell injection with either antisense [S]ODN JF2S (SEQ ID NO.: 4) (200 μg/mouse), control sense [S]ODN JF1S (SEQ ID NO.: 3) (200 μg/mouse) or PBS as diluent control. The mice were subsequently treated daily 6 times per week with either PBS as diluent control or antisense [S]ODN JF2S (SEQ ID NO.: 4) or control sense [S]ODN JF1S (SEQ ID NO.: 3) (100 μg of each [S]ODN/mouse in the experiment using MDA-MB-435 cells and 200 μg of each [S]ODN/mouse in the experiment using MCF-7 cells). The mice were checked for palpable tumors twice a week until sacrifice on day 28. FIG. 16 shows that all PBS diluent control (open circles)-and control sense [S]ODN JF1S (SEQ ID NO.: 3) (closed circles)-treated mice developed palpable tumors by day 17. In contrast, at that time tumors had developed in only 29% of the antisense [S]ODN JF2S (SEQ ID NO.: 4) (closed squares)-treated mice by day 17. On day 28, the day of termination of the experiment, 40% of the antisense [S]ODN JF2S (SEQ ID NO.: 4)-treated mice were still tumor-free. FIG. 17 shows that 100% of the PBS diluent control (open circles)-and control sense [S]ODN JF1S (SEQ ID NO.: 3) (closed circles)-treated mice developed palpable tumors by day 28, while only 22% of those mice treated with antisense [S]ODN JF2S (SEQ ID NO.: 4) (closed squares) exhibited palpable tumors at the time. Thus in vivo treatment with antisense [S]ODN JF2S (SEQ ID NO.: 4) delayed and in a subset of mice completely prevented the appearance of tumors from two different human breast tumor cell lines injected into athymic mice.

EXAMPLE IX

The efficacy of antisense [S]ODN JF2S (SEQ ID NO.: 4) in preventing tumor metastasis was investigated using an orthotopic model of human prostate cancer metastasis in athymic mice. Orthotopic tumor models are those in which tumor cells are implanted into the mouse organ equivalent to the source organ from which the tumor cell line is derived.

In the model used to test antisense [S]ODN JF2S (SEQ ID NO.: 4), the human prostate tumor cell line PC-3M (3.75× $10^5$ cells/mouse) was injected into one of the surgically exposed lobes of the prostate gland of an athymic mouse. The mouse was then treated 1 hour later by i.p. injection with either antisense [S]ODN JF2S (SEQ ID NO.: 4) (500 μg/mouse in the high dose group or 200 μg/mouse in the low dose group), control sense [S]ODN JF1S (SEQ ID NO.: 3) (500 μg/mouse in the high dose group or 200 μg/mouse in the low dose group), anti-angiogenin monoclonal antibody 26-2F (300 μg/mouse; included as a positive control treatment group, since it has been previously determined that this monoclonal antibody is efficacious in preventing PC-3M tumor metastasis in the same model), or PBS as diluent control. The [S]ODN-and PBS-treated mice were subsequently injected i.p. with the same materials at the same above doses per mouse daily 6 times per week from day 1–13, followed by injections of the same dose of the same materials 4 times per week until day 38. Monoclonal antibody 26-2F was administered on the same schedule but at a previously determined optimal dose of 180 μg/mouse for days 1–38. On day 39 the mice were sacrificed and the prostate examined for evidence of tumor. At that time all mice in the experiment contained a primary tumor in their prostate gland. The regional iliac lymph nodes were removed and preserved in phosphate-buffered formalin. These preserved lymph nodes were later dehydrated, embedded in paraffin, cut into 4 mm sections and stained with hematoxylin and eosin. The slides were then examined by a pathologist in a blinded fashion for evidence of metastasis. Table 2 below shows the results of this examination in terms of the number of mice in the indicated treatment group harboring metastasis in at least one of the two iliac lymph nodes divided by the total number of mice in the treatment group. This number is expressed as a percentage in parentheses below the aforementioned fraction.

TABLE 2

| | | Incidence of Metastasis | | | |
|---|---|---|---|---|---|
| PBS (diluent control) | mAb 26-2F (medium dose) | Sense control JF1S (high dose) | Antisense JF2S (high dose) | Sense control JF1S (low dose) | Antisense JF2S (low dose) |
| 6/6 (100%) | 4/9 (44%) | 9/9 (100%) | 5/10 (50%) | 6/6 (100%) | 4/5 (80%) |

All of the mice treated with PBS, a diluent control, or control sense [S]ODN JF1S (SEQ ID NO.: 3) (at both high and low doses) developed metastasis in at least one of the regional iliac lymph nodes. Monoclonal antibody 26-2F protected 56% of the mice from developing metastasis in the regional lymph nodes, a percentage comparable to that obtained in previous experiments. A low dose of antisense [S]ODN JF2S (SEQ ID NO.: 4) protected 1 out of the 5 mice from developing metastasis. However, the high dose of antisense [S]ODN JF2S (SEQ ID NO.: 4) protected 50% of the mice from forming regional lymph node metastasis. Thus antisense [S]ODN JF2S (SEQ ID NO.: 4) is effective in preventing human tumor metastasis in an orthotopic model of prostate tumor metastasis.

It is to be understood that the embodiments of the present invention which have been described are merely illustrative of some of the applications of the principles of the invention. Numerous modifications may be made by those skilled in the art based upon the teachings presented herein without departing from the true spirit and scope of the invention.

What is claimed is:

1. A method for inhibiting expression of human angiogenin in a human comprising administering to the human an effective amount of an oligonucleotide or analog thereof having a base sequence complementary to a target portion of a nucleic acid encoding human angiogenin so as to inhibit the expression of the angiogenin.

2. A method for reducing size of tumors associated with angiogenesis in a human comprising administering to the human an effective amount of an oligonucleotide or analog thereof having a base sequence complementary to a target portion of a nucleic acid encoding human angiogenin so as to reduce tumor size.

3. A method for decreasing production of human angiogenin in a human comprising administering to the human an effective amount of an oligonucleotide or analog thereof having a base sequence complementary to a target portion of a nucleic acid encoding human angiogenin so as to decrease production of the angiogenin.

4. A method for inhibiting metastasis of tumor cells in a human comprising administering to the human an effective amount of an oligonucleotide or analog thereof having a base sequence complementary to a target portion of a nucleic acid encoding human angiogenin so as to inhibit metastasis of tumor cells.

5. A method for inhibiting the establishment of tumor cells in a human comprising administering to the human an effective amount of an oligonucleotide or analog thereof having a base sequence complementary to a target portion of a nucleic acid encoding human angiogenin so as to inhibit establishment of tumor cells.

6. A method for inhibiting growth of tumors associated with angiogenesis in a human comprising administering to the human an effective amount of an oligonucleotide or analog thereof having a base sequence complementary to a target portion of a nucleic acid encoding human angiogenin so as to inhibit tumor growth.

7. A method for detecting the presence of human angiogenin in a human comprising administering to the human labeled oligonucleotide or analog thereof having a base sequence complementary to a target portion of a nucleic acid encoding human angiogenin;

allowing the labeled oligonucleotide or analog thereof to bind to the target portion of the nucleic acid encoding human angiogenin; and detecting the labeled oligonucleotide or analog thereof.

8. A method for diagnosing conditions associated with abnormal angiogenesis in a human comprising administering to the human a labeled oligonucleotide or analog thereof having a base sequence complementary to a target portion of a nucleic acid encoding human angiogenin;

allowing the labeled oligonucleotide or analog thereof to bind to the target portion of the nucleic acid encoding human angiogenin;

detecting the labeled oligonucleotide or analog thereof;

measuring the labeled oligonucleotide or analog thereof; and determining the abnormal condition based on the detecting and measuring of the labeled oligonucleotide or analog thereof.

* * * * *

SEQUENCE LISTING

```
<160> NUMBER OF SEQ ID NOS: 10

<210> SEQ ID NO 1
<211> LENGTH: 4668
<212> TYPE: DNA
<213> ORGANISM: Homo sapiens
<220> FEATURE:
<221> NAME/KEY: CDS
<222> LOCATION: (1809)..(2252)

<400> SEQUENCE: 1
tgtttgcatt aagttcatag attataattt gtaatggaat caacaccaaa tgcaaattag      60
aaagagagcc cactttgctc acccagtcac gtcttcccat gtaaccatag aacgttgggg    120
tcctgtgtct ttctagatcc acagtcttgc tctcagaaca ggctagccac accacaggcc    180
tagtgccagg acccatggcc ttttttttaag ctcagactcc cttctgtgaa cagcaatatc    240
cccacaactt gtacaacatt ggtgcttcct gcaagggcta cagaactatt tgatacgaaa    300
atgttcattg acttacacac aagagaagca caaaataaaa aattaataat taatttaatg    360
tctttgaaaa tgtaccattt atttttacat ttggggtcat aagaattgta ttacacttaa    420
gaatgcaata caatttgaag atcagatttt tctccctttg tgagaatttc tcagtatgtg    480
tgatgactac caagaaatca tagccagtca taaattcagt gagttactca taaacgaaca    540
agaaccacct acttcttggg gaggtaggtc tgcttccctt caactcagga tacaactgct    600
```

```
                                                          -continued ttcaactgct ttcttcacat tagctgacta attagctaga agcctgtcgt aaacaattt     660 atggttgact ccttccctgg gctcagggtt ccctagaaca gagaggtccc caaatcccgg    720
tctgtggcct gtccgcctaa gctctgcctc ctgccagatc agcaggcagc attagattct   780
cataggagct ggacgcctat tgtgaactgc gcatgtgcgg gatccagatt gtgcactctt   840
tatgagaatc taactaatgc ttgatgatct atctgaacca gaacaatttc atcctgaaac   900
catcccccac caatccatag aaatactgtc ttccacaaaa atgatccctg gtgccaaaaa   960
tgttagagac cactccccta aaactctctt cttagctctc acctcctgta ttactatctc   1020
atctcagtac attgaagccc ccatctttc cccatggatg cctcatttcc tattagggag    1080
gcattttttt attttttgtt tttatttttt tccgagacgg agtctcgctc tgtcgccaag   1140
gctggagtgc agtggcgcga tctcggctca ctgcaagctc cgcctccgg gttcacgcca    1200 ttctcctgcc tcagcctccc aagtagctgg gactacaggc gcccgcacta cgcccggcta   1260 atttttttgta ttttagtag agacggggtt tcaccgtggt agccaggatg gtctcgatct   1320
cctgacctcg tgatccgccc gccttggcct cccaaagtgc tgggattaca ggcgtgagac   1380
cgcgcccggc cgtcatttgg tatgtcttaa gtgtgcctcag gacctagcac agtccctggt   1440
acccagtaga gacctatgta atgttcgtta ttcaataata aatacatgaa ttaaagagtg   1500
agagtggatt ttgtaatgtt acgactgata gagaaatact cagtgattct aagggatggg   1560
gaagaacggt tggagctaga ggttgtgctc aggaaactat taaatagacg ttccgcagga   1620
agggattgac gaagtgtgag gttaatgagg aagggaaaat agaatataaa atttggtggt   1680
ggaaaagatc tgattcatga tgccgtgtca gagagcaaag ctcctgtcct tttggcctaa   1740
tttggtgatg ctgttcttgg gtctaccaca cctccttttg ccctccgcag gagcctgtgt   1800 tggaagag atg gtg atg ggc ctg ggc gtt ttg ttg ttg gtc ttc gtg ctg     1850
         Met Val Met Gly Leu Gly Val Leu Leu Leu Val Phe Val Leu
          1               5                   10 ggt ctg ggt ctg acc cca ccg acc ctg gct cag gat aac tcc agg tac     1898
Gly Leu Gly Leu Thr Pro Pro Thr Leu Ala Gln Asp Asn Ser Arg Tyr
 15                  20                  25                  30 aca cac ttc ctg acc cag cac tat gat gcc aaa cca cag ggc cgg gat     1946
Thr His Phe Leu Thr Gln His Tyr Asp Ala Lys Pro Gln Gly Arg Asp
                 35                  40                  45 gac aga tac tgt gaa agc atc atg agg aga cgg ggc ctg acc tca ccc     1994
Asp Arg Tyr Cys Glu Ser Ile Met Arg Arg Arg Gly Leu Thr Ser Pro
     50                  55                  60 tgc aaa gac atc aac aca ttt att cat ggc aac aag cgc agc atc aag     2042
Cys Lys Asp Ile Asn Thr Phe Ile His Gly Asn Lys Arg Ser Ile Lys
 65                  70                  75 gcc atc tgt gaa aac aag aat gga aac cct cac aga gaa aac cta aga     2090
Ala Ile Cys Glu Asn Lys Asn Gly Asn Pro His Arg Glu Asn Leu Arg
         80                  85                  90 ata agc aag tct tct ttc cag gtc acc act tgc aag cta cat gga ggt     2138
Ile Ser Lys Ser Ser Phe Gln Val Thr Thr Cys Lys Leu His Gly Gly
 95                 100                 105                 110 tcc ccc tgg cct cca tgc cag tac cga gcc aca gcg ggg ttc aga aac     2186
Ser Pro Trp Pro Pro Cys Gln Tyr Arg Ala Thr Ala Gly Phe Arg Asn
                115                 120                 125 gtt gtt gtt gct tgt gaa aat ggc tta cct gtc cac ttg gat cag tca     2234
Val Val Val Ala Cys Glu Asn Gly Leu Pro Val His Leu Asp Gln Ser
                130                 135                 140 att ttc cgt cgt ccg taa ccagcgggcc cctggtcaag tgctggctct            2282
Ile Phe Arg Arg Pro
        145
```

```
gctgtccttg ccttccattt ccctctgca cccagaacag tggtggcaac attcattgcc    2342
aagggcccaa agaaagagct acctggacct tttgttttct gtttgacaac atgtttaata    2402
aataaaaatg tcttgatatc agtaagaatc agagtcttct cactgattct ggcatattg    2462 atctttcccc catttctct acttggctgc tccctgagag gactgcatag gatagaaatg    2522
ccttttcttt ttcttttcgt tttttttttt tttttttttt gagatggagt ctcactctgt    2582
cgcccaggct taagtgcaat ggcacaatct cggctcactg caacctctct ctcctgggtt    2642
caagtgattc tcctgcctca gcctcccaaa tagctgagat tacaggcatg caccaccaca    2702
cctggctaat ttttgtgttt ttagtagaga cagggtttca ccgttttggc caggttggtc    2762
ttgaactcct gacctcggga gatccgccca ccttggcctc tctttgtgct gggattacag    2822
gcatgagcca ctgagccggg ccacttttc cttatcagtc agtttttaca agtcattagg    2882
gaggtagact ttacctctct gtgaaggaaa gtatggtatg ttgatctaca gagagagatg    2942
gaaaaattcc agggctcgta gctactaagc agaatttcca agataggcaa attgttttt    3002 ctgtcaaata ataagctaat attacttcta caaatatgag accttggaga gaagtttcca    3062
aggaccaagt accaacatac caacagatta ttatagtttc tctcactctt acacacacac    3122
acacacatat acacatatgt aatccagcat gaataccaaa attcattcag ggtagccacc    3182
ttttgtctta atcgagagat aattttgatg tttgaatgga atgctcccag gatattctct    3242
tgtcatggtt attttatata aaattcaaaa accaattaca ttatttcctc tgtaatcttt    3302
tactttatca actaatgtct ggcaagtgtg atgttttggg gaagttatag aagattccgg    3362
ccaggcgctt atctcacgct tgtaatccag cactttggga agctgaggcg gacagatcac    3422
gaggtcaaga gatcaagacc atcctggaca acatggtgaa accttgtctc tactaaaaat    3482
gtgaaaatta ctgggcgtg gtggcacaca cctatagtcc cagctactcg ggaggctgag    3542
gcaggagaat cgcttgaacc taggaggcgg aggttgcact gagccgagat cacgccactg    3602
cactccagcc tgggcgacag agcgagactc catctcaaaa aaaaaaaaaa aagaaagatc    3662
ccagtttatc ccagtttatc ccttattctt cctcaattct caagatttgt ttttaagtta    3722
acataactta ggttaacaca ctctttgtaa aatacactgt tcaatctaca gactcagtgg    3782
ttagcttcct gttaactaat ttctgttgac aggtacttgg atattttatt tagaaagtgg    3842
ttgccaataa attagttata agtcgccagt ttcactgcct tgtgaacaca taattattgt    3902
ggtctcagta ttccctatgg tggcttctcc tgctcctggt attgccctga aatgggccaa    3962
aagccgtggc tccccaatgc tcaggttata gaacattgtc caggtaccac ctaggagagc    4022
ccagcctcac tgaaagtatt caaatttagg aatgggtttg agaagtaggt agctggtatg    4082
tgcttagcac aagaatctct cttccttggg ttagtctgtt tcaaaactga aaacactgtc    4142
attccttaag aaaataggaa aaagtattcc aaacctctgt cactagaaaa tttgccatat    4202
taccaaatct caaaaacctc tcaggaaatg agaaagtccc agtttctggt aaactatttg    4262
ggcccttttc tcaagttctc cttccagtgc tatttccttg aggtgaggca agttactca    4322 agatcatcgc tgccactcaa ggccttgata gggcaagtga aaggcatgga ccattattat    4382
attgatcaca gcataagctg tgaaaaccca catcttctcc aaacatctgc ttggagcatt    4442
atcatcgcat agtttgctct ggtgttcagg gaaatcgctg tttcatagga aatcacatgg    4502
cagtgggatg ggagtgtttc ctgacctgcc gatggtactg gcacctgagc aagcattcct    4562
agtccttttt ggtctgggcc tcttgttcta tcacaaccac aagctgttta aataaaaac    4622
```

```
gtcaagtcac aggcaggtca ttttatcctg cgtgaatcaa ttgaag                    4668
```

<210> SEQ ID NO 2
<211> LENGTH: 147
<212> TYPE: PRT
<213> ORGANISM: Homo sapiens

<400> SEQUENCE: 2

| Met | Val | Met | Gly | Leu | Gly | Val | Leu | Leu | Leu | Val | Phe | Val | Leu | Gly | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Gly Leu Thr Pro Pro Thr Leu Ala Gln Asp Asn Ser Arg Tyr Thr His
            20                  25                  30

Phe Leu Thr Gln His Tyr Asp Ala Lys Pro Gln Gly Arg Asp Asp Arg
        35                  40                  45

Tyr Cys Glu Ser Ile Met Arg Arg Gly Leu Thr Ser Pro Cys Lys
    50                  55                  60

Asp Ile Asn Thr Phe Ile His Gly Asn Lys Arg Ser Ile Lys Ala Ile
65                  70                  75                  80

Cys Glu Asn Lys Asn Gly Asn Pro His Arg Glu Asn Leu Arg Ile Ser
                85                  90                  95

Lys Ser Ser Phe Gln Val Thr Thr Cys Lys Leu His Gly Gly Ser Pro
            100                 105                 110

Trp Pro Pro Cys Gln Tyr Arg Ala Thr Ala Gly Phe Arg Asn Val Val
        115                 120                 125

Val Ala Cys Glu Asn Gly Leu Pro Val His Leu Asp Gln Ser Ile Phe
    130                 135                 140

Arg Arg Pro
145

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      phosphorothioate oligodeoxynucleotide

<400> SEQUENCE: 3

```
gaagagatgg tgatgggc                                                    18
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      phosphorothioate oligodeoxynucleotide

<400> SEQUENCE: 4

```
gcccatcacc atctcttc                                                    18
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:
      phosphorothioate oligodeoxynucleotide

<400> SEQUENCE: 5

```
acacggcatc atgaatca                                                    18
```

```
<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:
      phosphorothioate oligodeoxynucleotide

<400> SEQUENCE: 6 ccagggccc gctggtta                                                 18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      phosphorothioate oligodeoxynucleotide

<400> SEQUENCE: 7
accaaatttt atattcta                                                18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      phosphorothioate oligodeoxynucleotide

<400> SEQUENCE: 8
caggcccatc accatcac                                                18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:
      phosphorothioate oligodeoxynucleotide

<400> SEQUENCE: 9
gcccaggccc atcaccat                                                18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:
      phosphorothioate oligodeoxynucleotide

<400> SEQUENCE: 10
tctctgacac ggcatcat                                                18
```